US006735531B2

(12) United States Patent
Rhett et al.

(10) Patent No.: US 6,735,531 B2
(45) Date of Patent: May 11, 2004

(54) METHOD AND APPARATUS FOR AUTOMATIC TISSUE STAINING

(75) Inventors: Norman K. Rhett, San Ramon, CA (US); Ken K. Tseung, Fremont, CA (US); Mark V. Corl, Castro Valley, CA (US); Wai Bun Wong, Fremont, CA (US); Ngoc Van Le, Milpitas, CA (US); Glenn K. Takayama, Danville, CA (US)

(73) Assignee: Lab Vision Corporation, Fremont, CA (US)

( * ) Notice: Subject to any disclaimer, the term of this patent is extended or adjusted under 35 U.S.C. 154(b) by 105 days.

(21) Appl. No.: 10/010,830

(22) Filed: Nov. 13, 2001

(65) Prior Publication Data

US 2002/0116132 A1 Aug. 22, 2002

Related U.S. Application Data

(63) Continuation-in-part of application No. 09/133,292, filed on Aug. 12, 1998, now Pat. No. 6,349,264, which is a continuation of application No. 08/726,702, filed on Oct. 7, 1996, now Pat. No. 5,839,091.

(51) Int. Cl.[7] ................................................ G01N 33/53
(52) U.S. Cl. .............................. 702/31; 702/19; 422/63; 422/67
(58) Field of Search ............................... 702/31, 19, 22, 702/25, 4.27, 30–32, 183, FOR 170, FOR 134, FOR 14, FOR 115–FOR 119; 435/283.1, 286.1, 287.1, 286.4, 287.2, 287.3, 287.9, 288.7, 970, 973, 40.32; 422/63, 65, 67, 68.1, 30, 62; 436/63, 43, 46, 174, 807, 808; 700/266

(56) References Cited

U.S. PATENT DOCUMENTS 4,141,312 A  2/1979  Louder et al. .............. 118/702

5,073,504 A  12/1991  Bogen ........................ 436/174
5,116,759 A  5/1992  Klainer et al. ............ 435/287.2

(List continued on next page.)

FOREIGN PATENT DOCUMENTS

| WO | WO9113335  | 9/1991  |             |
|----|------------|---------|-------------|
| WO | WO9201919  | 2/1992  |             |
| WO | WO 99/10763| * 3/1999|             |
| WO | WO01/51909 | 7/2001  | G01N/1/31   |
| WO | WO01/68259 | 9/2001  | B01L/3/02   |

OTHER PUBLICATIONS

BioGenex, *Optimax TM Automated Cell Staining System*, 4 pages. (No date).
Biotek TM Solutions, *Automated Immunostaining Systems*, 1993, 12 pages (No month).
Hamilton, *MicrolabRTM SPE*, 1 page (No date).

(List continued on next page.)

*Primary Examiner*—Hal Wachsman
(74) *Attorney, Agent, or Firm*—Wood, Herron & Evans LLP

(57) ABSTRACT

To simplify the process of preparing microscope slides, an automatic staining apparatus is disclosed. The disclosed automatic staining apparatus comprises an electromechanical automatic staining device that is coupled to a personal computer system using an interface card. An autostainer control program runs on the personal computer system. The autostainer control program allows a user to simply program the automatic staining apparatus using simple commands entered in the graphical user interface. The autostainer control program includes several features that simplify the programming such as safeguards that ensure compatible reagents are being used; automatic buffer solution requirement calculator; and the ability to determine optimal staining procedure. The electromechanical automatic staining device includes features such as dual waste bins for hazardous and nonhazardous waste storage, an automatic dispenser cleansing system; and a slide clip that minimizes capillary effect.

19 Claims, 41 Drawing Sheets

U.S. PATENT DOCUMENTS

| | | | | |
|---|---|---|---|---|
| 5,350,564 | A | * | 9/1994 | Mazza et al. ................. 422/63 |
| 5,355,439 | A | | 10/1994 | Bernstein et al. ........... 700/247 |
| 5,425,918 | A | | 6/1995 | Healey et al. ................ 422/64 |
| 5,428,690 | A | | 6/1995 | Bacus et al. ................ 382/128 |
| 5,439,649 | A | | 8/1995 | Tseung et al. ................ 422/99 |
| 5,559,032 | A | | 9/1996 | Pomeroy et al. ......... 435/289.1 |
| 5,573,727 | A | | 11/1996 | Keefe .......................... 422/63 |
| 5,595,707 | A | | 1/1997 | Copeland et al. ............. 422/64 |
| 5,650,327 | A | | 7/1997 | Copeland et al. ............. 436/46 |
| 5,654,199 | A | | 8/1997 | Copeland et al. ............. 436/46 |
| 5,654,200 | A | | 8/1997 | Copeland et al. ............. 436/46 |
| 5,696,887 | A | | 12/1997 | Bernstein et al. ........... 700/247 |
| 5,839,091 | A | | 11/1998 | Rhett et al. ................... 702/19 |
| 5,919,553 | A | | 7/1999 | Kavanaugh ................. 428/195 |
| 5,930,461 | A | | 7/1999 | Bernstein et al. ........... 700/247 |
| 5,948,359 | A | | 9/1999 | Kalra et al. ................... 422/65 |
| 6,045,759 | A | | 4/2000 | Ford et al. .................. 422/103 |
| 6,090,630 | A | * | 7/2000 | Koakutsu et al. ............. 436/50 |
| 6,093,574 | A | | 7/2000 | Druyor-Sanchez et al. . 436/180 |
| 6,192,945 | B1 | | 2/2001 | Ford et al. ...................... 141/2 |
| 6,296,809 | B1 | | 10/2001 | Richards et al. .............. 422/64 |
| 6,352,861 | B1 | | 3/2002 | Copeland et al. ............. 436/46 |
| 6,498,037 | B1 | * | 12/2002 | Carey et al. ................... 436/50 |

OTHER PUBLICATIONS

Leica, *Automated Tissue Staining for Immunohistochemistry*, Feb. 6, 1992, 8 pages.

Matrix Technologies Corporation, *Automated Sample Handling*, Sep. 1993, 4 pages.

Packard, *MultiprobeRTM Robotic Liquid Handling*, newsletter and pp. 8–9, (No date).

Rosys, *Introduce a new philosophy into your laboratory*, 1 page.

Sakura World Class Technology TM, *RSG–61 Hematology Slide Stainer*, 1995, 2 pages. (No month).

Shandon Cadenza RTM, *Automated Immunostainer*, 1989, pp. 1–8, (No month).

Tecan US, Inc., *Progressing as One in Laboratory Automation*, brochure, 9 pages, (No date).

Ventana, *Ventana in Situ Hybridization System*, Rev–Mar. 31, 1994, 1 page.

* cited by examiner

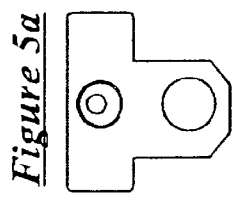
*Figure 5a*
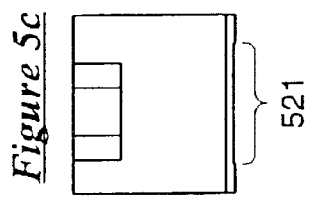
*Figure 5c*
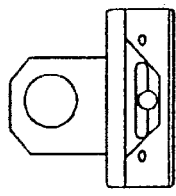
*Figure 5f*
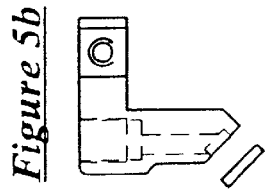
*Figure 5b*
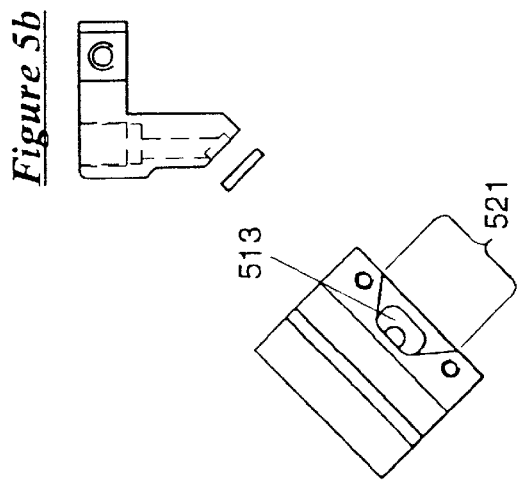
*Figure 5d*
*Figure 5e*

| Program Staining Run | | | | | | | |
|---|---|---|---|---|---|---|---|
| File  Edit lists  Copy  Auto | | | | | | | |
| Slide # | Patient Name Case # | Doctor Name | Rinse | End Enz. Block 200 µl | Rinse | Pretreatment Antibody 200 µl | Rinse | Primary Antibody 200 µl | Rinse | Secondary Reagent 200 µl |
| 1 | | | | | | | |
| 2 | | | | | | | |
| 3 | | | | | | | |
| 4 | | | | | | | |
| 5 | | | | | | | |
| 6 | | | | | | | |
| 7 | | | | | | | |

Program:

| Patient Info ~910 | Protocol Template ~920 | Run ~930 | Print ~940 | Exit ~950 | Help ~960 |

*Figure 9a*

Program Staining Run

File  Edit lists  Copy  Auto

| Slide # | Patient Name Case # | Doctor Name | Pretreatment 200 μl | Rinse | Primary Antibody 200 μl | Rinse | Secondary Reagent 200 μl | Rinse | Tertiary Reagent 200 μl |
|---|---|---|---|---|---|---|---|---|---|
| 41 | a, a | Dr. Mark | | ◊ | Calci 10' | ◊ | BixMxR 10' | ◊ | SA-HRP 10' |
| 42 | a, a | Dr. Mark | | ◊ | NCCalc 10' | ◊ | BixMxR 10' | ◊ | SA-HRP 10' |
| 43 | a, a | | | | | | | | SA-HRP 10' |
| 44 | a, a | | | | | | | | SA-HRP 10' |
| 45 | a, a | | | | | | | | SA-HRP 10' |
| 46 | a, a | Dr. Mark | | ◊ | VimV9 10' | ◊ | BixMxR 10' | ◊ | SA-HRP 10' |
| 47 | a, a | Dr. Mark | | ◊ | NCV9 10' | ◊ | BixMxR 10' | ◊ | SA-HRP 10' |

Which Report?

[ Main Grid ]  [ I.H.C. ]  [ Cancel ]

Program: canada-1

[ Patient Info ] [ Protocol Template ] [ Run ] [ Print ] [ Exit ] [ Help ]

*Figure 9b*

Patient Information

Enter last name or last, first mi

Patient Name: John, Smith ▶ —1011
Patient Case #: 12345 ▶ —1081
Slides/case: 48 ▶ —1040
Doctor: Dr. Mark Corl 1010— Finish Entry  1020—Delete  1030—Cancel  Help You have now entered: 1 patient(s) 1 case(s) 48 slides

Program Staining Run

File  Edit lists  Copy  Auto

| Slide # | Patient Name Case # | Doctor Name | R i n s e | Primary Antibody 200 µl | R i n s e | Secondary Reagent 200 µl | R i n s e | Tertiary Reagent 200 µl | R i n s e | R W C h | Substrate 200 µl |
|---|---|---|---|---|---|---|---|---|---|---|---|
| 41 | John Smith 12345 | Dr. Mark | ⚪ | PSA-m 10' | ⚪ | BixMxR 10' | ⚪ | SA-HRP 10' | ⚪ | ⊠ | DAB 3' |
| 42 | John Smith 12345 | Dr. Mark | ⚪ | S-100 | ⚪ | BixMxR | ⚪ | SA-HRP | ⚪ | ⊠ | DAB 3' |
| 43 | John Smith 12345 | | | | | | ⚪ | HRP | ⚪ | ⊠ | DAB 3' |
| 44 | John Smith 12345 | | | | | | ⚪ | HRP | ⚪ | ⊠ | DAB 3' |
| 45 | John Smith 12345 | | | | | | ⚪ | HRP | ⚪ | ⊠ | DAB 3' |
| 46 | John Smith 12345 | Dr. Mark | ⚪ | Kappam 10' | ⚪ | BixMxR 10' | ⚪ | SA-HRP 10' | ⚪ | ⊠ | DAB 3' |
| 47 | John Smith 12345 | | | | | | | | | | |

Incompatible Reagents

AEC is incompatible with Strepatavidin-AP.

Continue?

[Yes]  [No]

Program: canada-1

[Patient Info]  [Protocol Template]  [Run]  [Print]  [Exit]  [Help]

*Figure 16*

| Slide # | Patient Name Case # | Doctor Name | Rinse | Primary Antibody 200 µl | Rinse | Secondary Reagent 200 µl | Rinse | Tertiary Reagent 200 µl | Rinse | SW-iCh | Substrate 200 µl |
|---|---|---|---|---|---|---|---|---|---|---|---|
| 41 | John Smith 12345 | Dr. Mark | | PSA-m 10' | | BixMxR 10' | | SA-HRP 10' | | | DAB 3' |
| 42 | John Smith 12345 | Dr. Mark | | S-100 10' | | BixMxR 10' | | SA-HRP 10' | | | DAB 3' |
| 43 | John Smith 12345 | Dr. Mark | | OPD4 | | BixMxR | | SA-HRP | | | DAB 3' |
| 44 | John Smith 12345 | Dr. | | | | | | RP | | | DAB 3' |
| 45 | John Smith 12345 | Dr. | | | | | | RP 10' | | | DAB 3' |
| 46 | John Smith 12345 | Dr. | | Kappam 10' | | BixMxR 10' | | RP 10' | | | DAB 3' |
| 47 | John Smith 12345 | Dr. Mark | | 10' | | 10' | | SA-HRP 10' | | | DAB 3' |

Run program now
Save program on disk
Yes | No | Cancel

Program: canada-1

Patient Info | Protocol Template | Run | Print | Exit | Help

Run Log

Current Program: canada-1

```
00:10:00- Treat slide 44 (1) with 200μl
00:10:00- Treat slide 45 (2,3) with 200μl
00:10:00- Treat slide 46 (1) with 200μl
00:10:00- Clean probe
00:10:00- Wait until 00:18:48
00:18:48- Rinse slide 25
00:18:48- Rinse slide
00:18:48- Rinse slide
00:18:48- Rinse slide
00:18:48- Rinse slide
00:18:48- Wait until 0
00:20:34- Rinse slide 32
00:20:34- Rinse slide 33
00:20:34- Rinse slide 34
00:20:34- Rinse slide 35
00:20:34- Wait until 00:21:44
04:27  00:21:42
```

Are you sure?
Stop run now
[Yes] [No]  ~2715

Elapsed  0:00
Remain   4:27
Total    4:27

Start    4:42 PM
Current  4:43 PM
Finish   9:09 PM

Emergency Stop ~2710    End

*Figure 27*

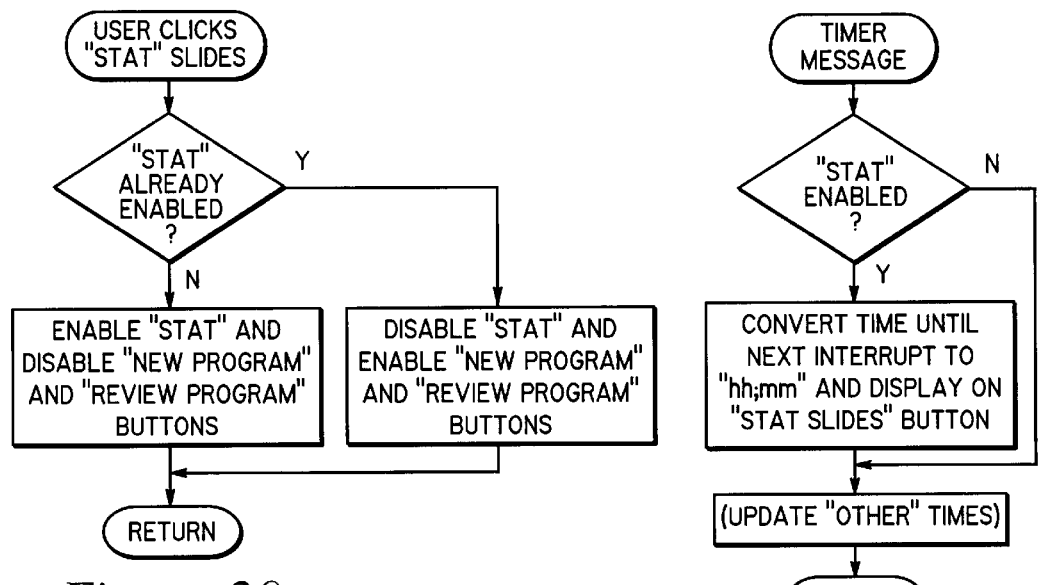
*Figure 29*
*Figure 30*
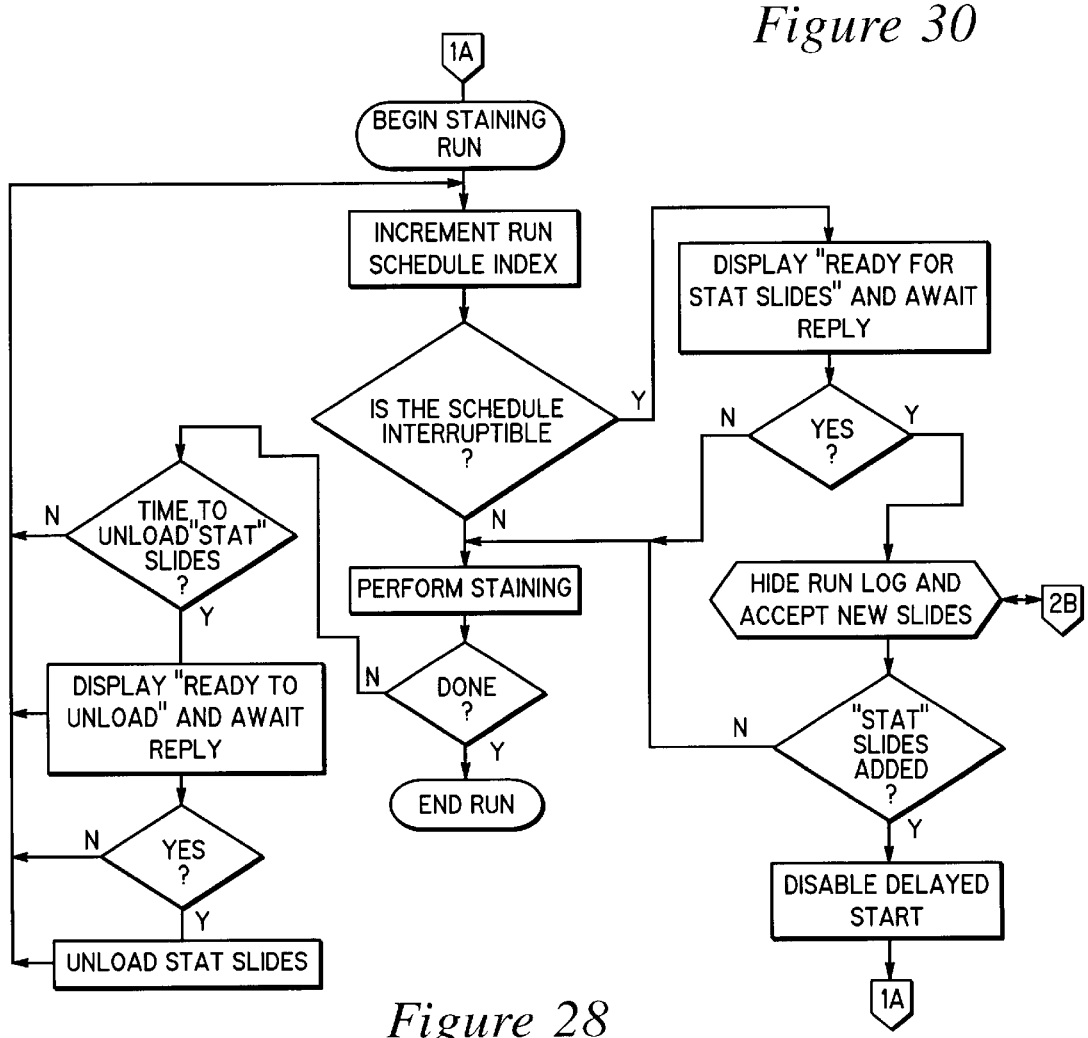
*Figure 28*

METHOD AND APPARATUS FOR AUTOMATIC TISSUE STAINING

This is a Continuation-In-Part of U.S. application Ser. No. 09/133,292, filed Aug. 12, 1998, now U.S. Pat. No. 6,349,264, which is a Continuation of U.S. application Ser. No. 08/726,702, filed Oct. 7, 1996, now U.S. Pat. No. 5,839,091, each of which is expressly incorporated by reference herein in its entirety.

FIELD OF THE INVENTION

The present invention relates to the field of medical lab equipment. In particular the present invention discloses a fully automated system for staining tissue specimens and cell preparations.

BACKGROUND OF THE INVENTION

It is often difficult to examine unstained cell and tissue preparations with a microscope due to a lack of contrast between individual cells and the background matrix, or between individual parts of cells. To improve the contrast, researchers have applied stains to cell and tissue specimens to be examined. The stains are absorbed differently by the various structures in cells such that the contrast between the different cell structures is improved.

Staining tissue specimens is a nontrivial time-consuming process. Often a number of different staining and rinsing stages are required. Each stage requires a specific amount of reagent or buffer and takes a specific amount of time. Thus, trained technicians are often employed to perform such operations. Furthermore, hospitals and laboratories must stain large numbers of tissue specimens. Thus, it is desirable to automate the tissue specimen staining process. By automating the process, expensive human labor is eliminated and the probability of an error occurring during the staining process is reduced. Accordingly, a few manufacturers have introduced equipment for the automated staining of tissue specimens on microscope slides.

Existing automatic staining devices are not very simple to use. Arcane programming commands and complicated procedures require extensive user training before such devices can be operated effectively. It would therefore be desirable to simplify the operation of an automatic staining device.

SUMMARY OF THE INVENTION

The present invention comprises an automatic staining apparatus coupled to a personal computer system running an operating system with a graphical user interface. The personal computer system includes an interface card that is used to control the automatic staining apparatus. An autostainer control program runs on the personal computer system. The autostainer control program allows a user to simply program the automatic staining apparatus using simple commands entered in the graphical user interface. The autostainer control program also includes a Stat function that allows the user to interrupt the routine staining of slides in order to prioritize processing of one or more slides that require immediate analysis. The invention simplifies the process of programming an automatic staining apparatus to include staining of stat slides.

Other objects, features, and advantages of present invention will be apparent from the accompanying drawings and detailed description.

BRIEF DESCRIPTION OF THE DRAWINGS

The objects, features and advantages of the present invention will be apparent to one skilled in the art, in view of the following detailed description in which:

FIG. 5a illustrates a top view of the air nozzle.

FIG. 5b illustrates a left side external view of the air nozzle and the nozzle lip.

FIG. 5c illustrates a front view of the air nozzle.

FIG. 5d illustrates a right side cutaway view of the air nozzle and the nozzle lip.

FIG. 5e illustrates a view of the air nozzle tip.

FIG. 5f illustrates a bottom view of the air nozzle.

FIG. 9a illustrates the Program Staining Run Screen of the autostainer control program.

FIG. 9b illustrates the Program Staining Run Screen with a Print Report dialogue box displayed.

FIG. 10 illustrates the Patient Information Screen of the autostainer control program.

FIG. 12 illustrates an Edit Individual Slide Reagent Screen of the autostainer control program.

FIG. 13 illustrates the Edit Individual Slide Reagent Screen of FIG. 12 with the fields filled in.

FIG. 14 illustrates the Program Staining Run Screen of the autostainer control program with an auto programming pop-up window displayed.

FIG. 15 illustrates the Program Staining Run Screen of the autostainer control program with a Detection Kit list for a selected Detection Kit step.

FIG. 16 illustrates the Program Staining Run Screen of the autostainer control program with an incompatible reagent warning dialogue box.

FIG. 18 illustrates the Program Staining Run Screen with a Save Current Program dialogue box.

FIG. 19 illustrates the Slide Layout Map Screen of the autostainer control program.

FIG. 24 illustrates the Reagent Layout Map Screen of the autostainer control program.

FIG. 27 illustrates the Run Log Screen of the autostainer control program.

FIG. 28 illustrates a program initiating the Stat function.

FIG. 29 illustrates a Timer Message for the Stat function.

FIG. 30 illustrates the initial steps in implementing a Stat staining program.

DETAILED DESCRIPTION OF THE PREFERRED EMBODIMENT

A method and apparatus for automatically staining tissue specimens are disclosed. In the following description, for purposes of explanation, specific nomenclature is set forth to provide a thorough understanding of the present invention. However, it will be apparent to one skilled in the art that these specific details are not required in order to practice the present invention. For example, the present invention has been described with reference to staining of tissue specimens. However, the same techniques can easily be applied to other types of slide preparation work. Also as known to one skilled in the art, staining includes application of reagents to effect immunological as well as biochemical reactions, and thus is defined broadly.

The Autostainer Hardware

Figure 1A:
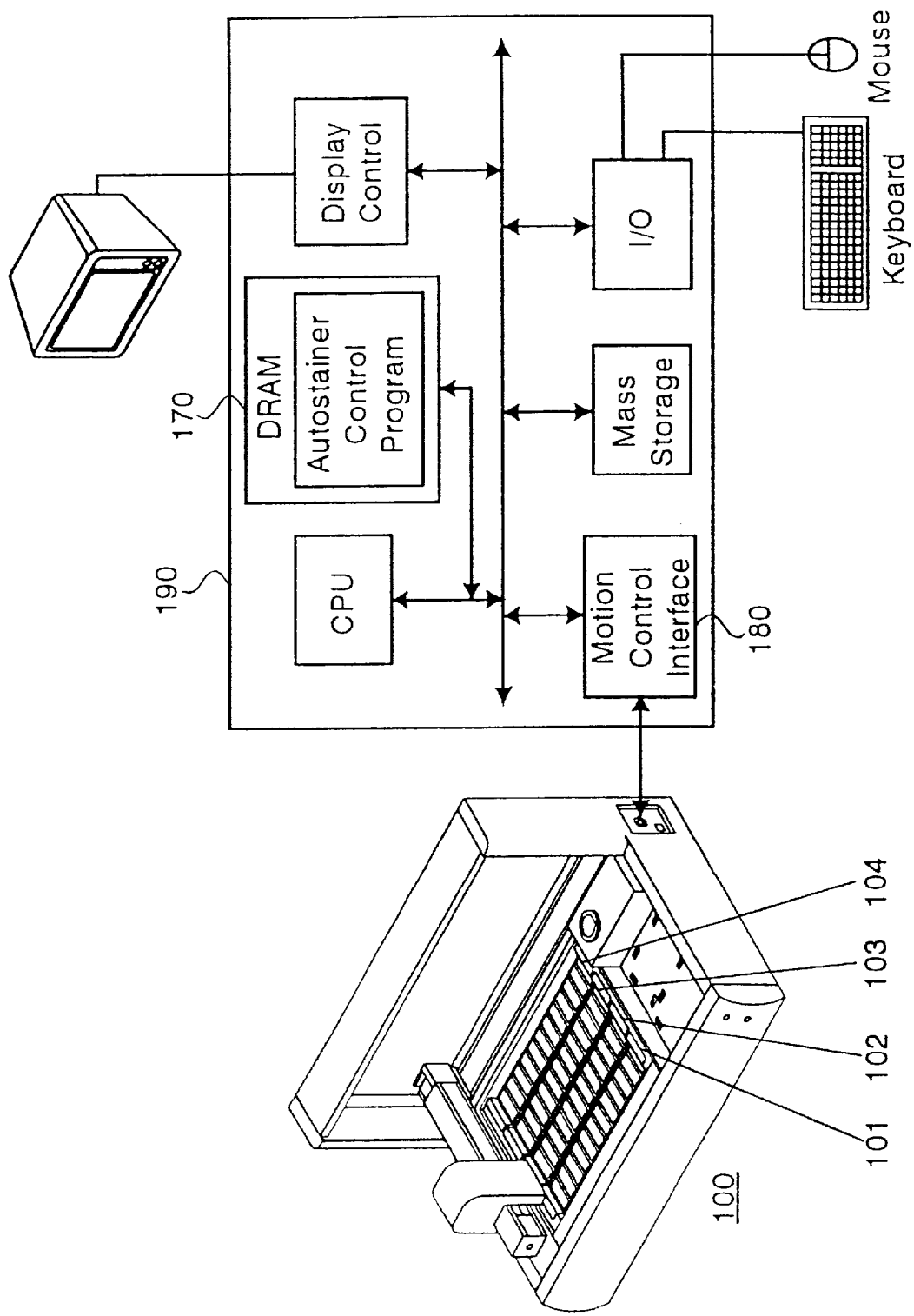
FIG. 1a illustrates a perspective view of the autostainer 100 apparatus.

FIG. 1a illustrates a perspective view of the autostainer 100 apparatus of the present invention. The autostainer 100 is used for staining tissue specimens that are placed onto glass slides. In the embodiment illustrated in FIG. 1a, there are four slide racks 101, 102, 103, and 104. Each slide rack is capable of holding twelve slides such that the autostainer 100 of FIG. 1a can perform operations on forty-eight slides at once.

The autostainer 100 of FIG. 1a has a robotic delivery system that delivers reagents, buffer solutions, and air to the glass slides. The robotic delivery system is controlled by a motion control interface card 180 in a personal computer system 190. The personal computer system 190 runs an autostainer control program 170 that sends control commands through the motion control interface 180 to control the robotic delivery system.

Figure 1B:
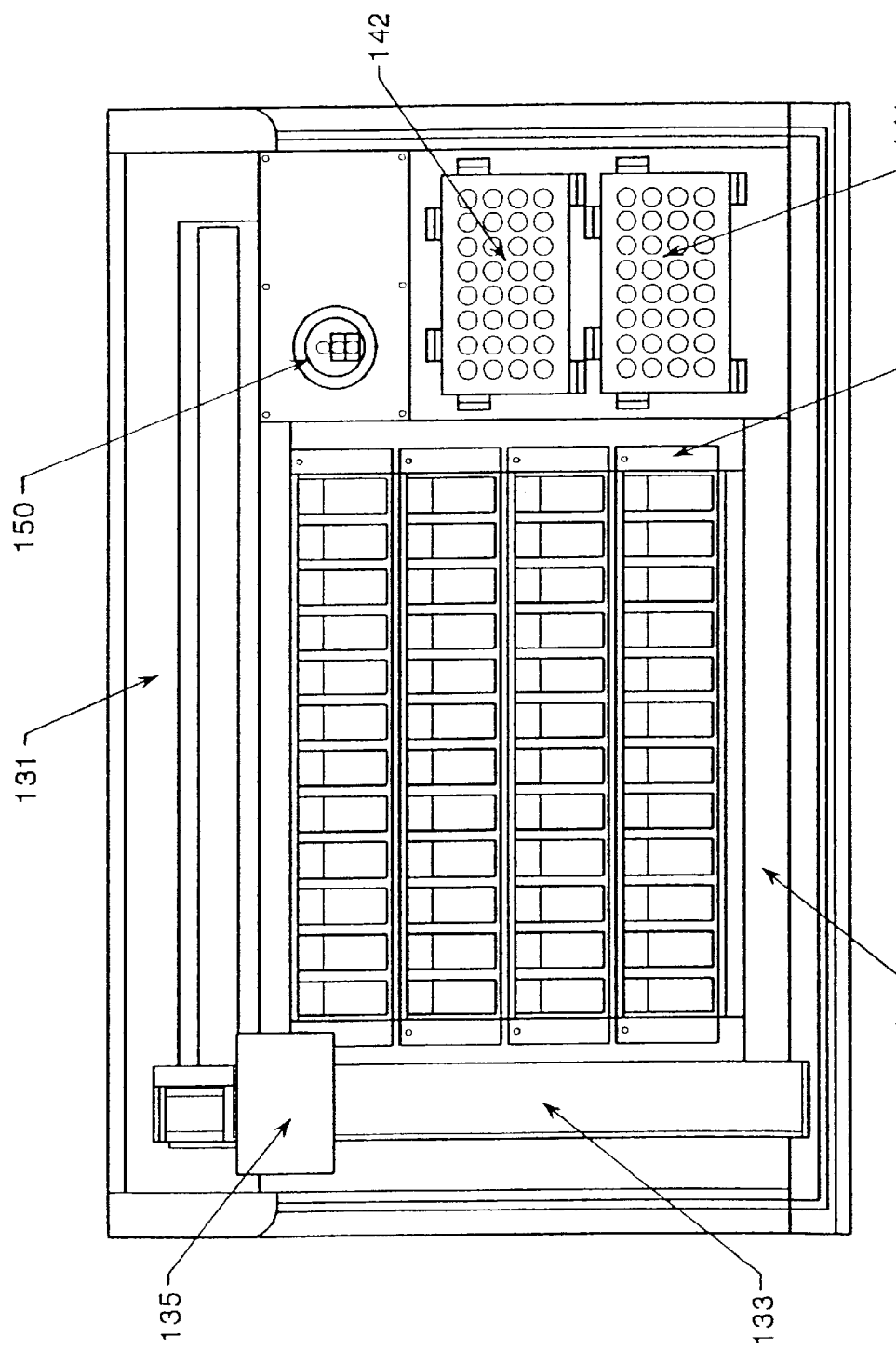
FIG. 1b illustrates a top view of the autostainer 100 apparatus.

FIG. 1b illustrates a top view of the autostainer 100. Referring to FIG. 1b, the robotic delivery system of the autostainer 100 consists of an X axis mechanism 131, a Y axis mechanism 133, and a Z head 135. The Z head 135 has a buffer tube for dispensing buffer rinse solution, a blow nozzle to blow air onto slides, and a probe for picking up reagents that will be placed onto the glass slides. The various reagents are stored in the reagent racks 141 and 142.

To prevent contamination, the probe is cleaned in a reagent probe wash bin 150 between the use of different reagents. The wash bin 150 has three different receptacles that are used in three stages. The first hole is used to rinse the inside of the probe by forcing buffer rinse solution through the inside of the probe and down into a first drain receptacle. The second receptacle is used to clean the outside of the probe by forcing buffer rinse solution through the inside of the probe while the probe is in the tightly confined second receptacle such that the buffer solution is forced upward on the outside of the probe. Finally, the probe is placed into a third receptacle and air is forced through the probe to clean out the buffer rinse solution.

Figure 2:
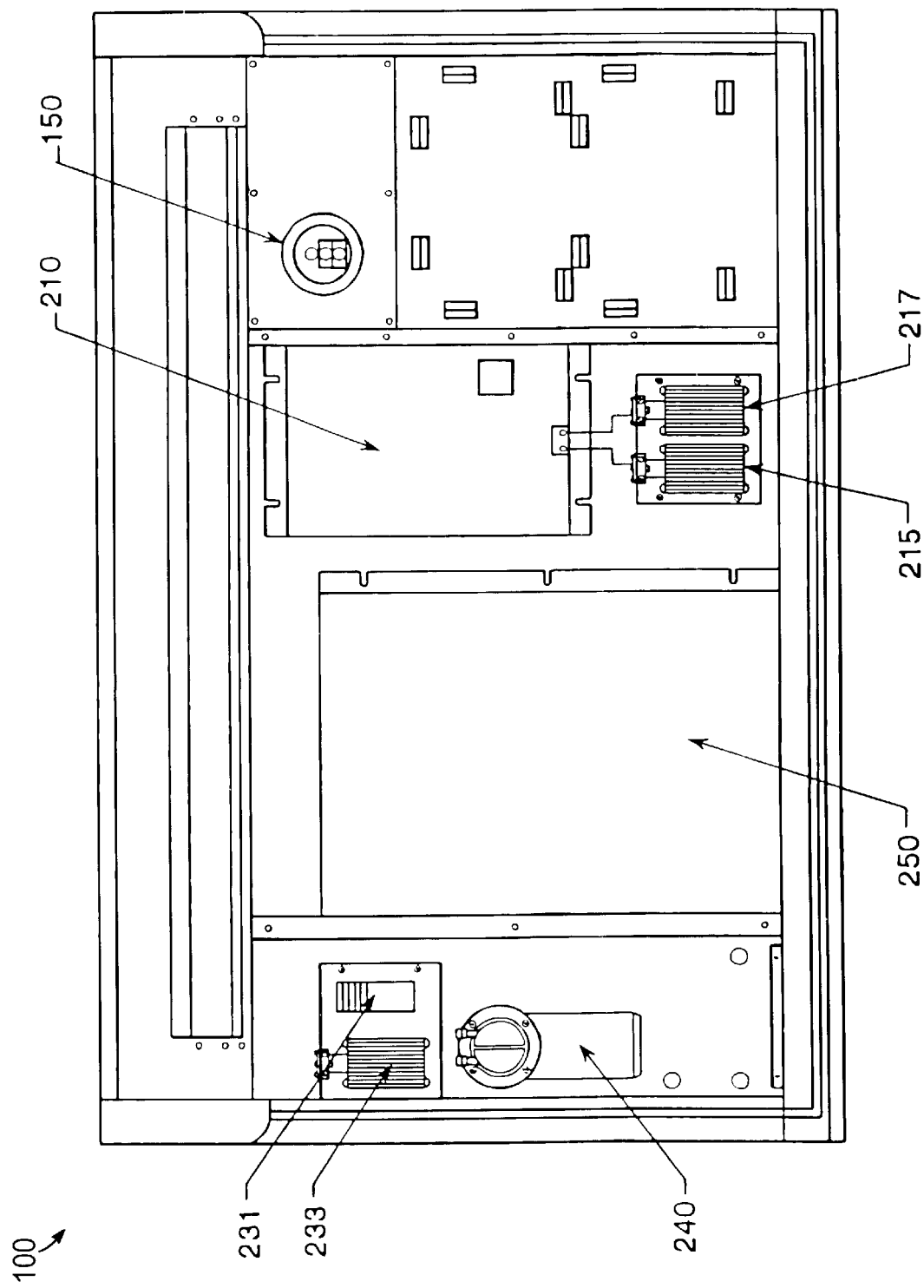
FIG. 2 illustrates a cut-away top view of the internal components of the autostainer 100 apparatus.

Beneath the slide racks of the autostainer 100 is a sink assembly 110. The sink assembly catches the reagents and buffer rinse solution that drip off the slides. FIG. 2 illustrates a cut-away top view of the internal components of the autostainer 100 apparatus. As illustrated in FIG. 2, a waste reservoir 210 that sits beneath the sink assembly collects the waste. The waste is pumped out of the waste reservoir 210 using a first waste pump 215 or a second waste pump 217. Two different waste pumps are used such that one waste pump is used to remove nonhazardous waste and the other waste pump is used to remove hazardous waste.

Several other components are also located inside the autostainer. Referring to FIG. 2 a buffer valve 231 and a buffer pump 233 are used to provide buffer rinse solution to the Z head assembly. An air compressor 240 is used to provide compressed air to the Z head assembly. An electronic controller box 250 stores a set of electronic components including the stepper motor drivers for the X, Y, and Z axes.

Autostainer Slide Racks

Figure 3A:
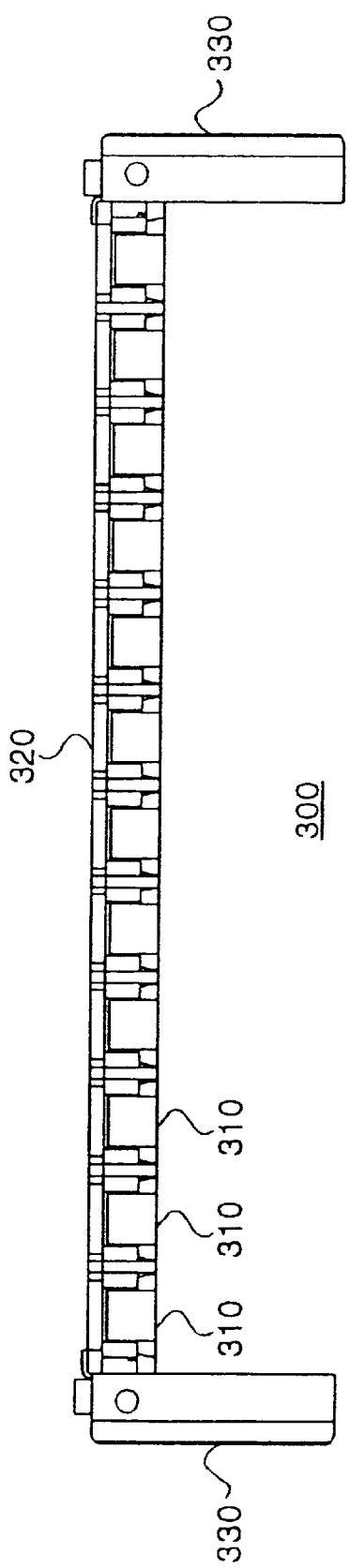
FIG. 3a illustrates a top view of a slide rack for the autostainer.
Figure 3B:
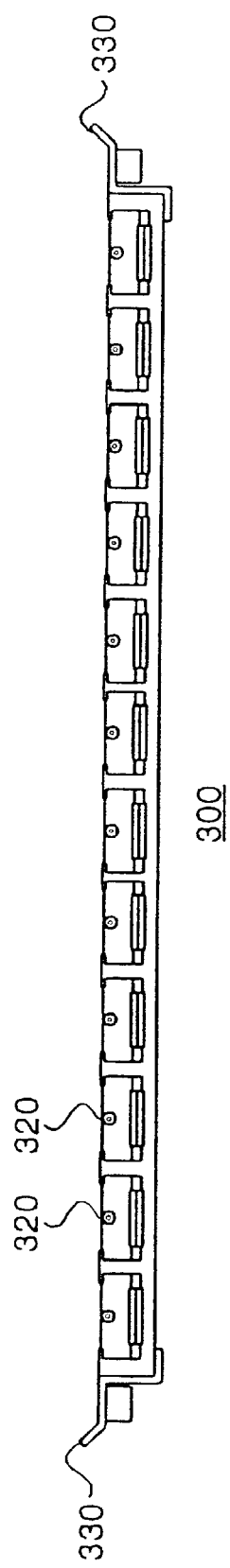
FIG. 3b illustrates a front view of a slide rack for the autostainer.

The slide racks for the autostainer of the present invention have been designed for optimum performance. FIG. 3a illustrates a top view of a slide rack that is used in the autostainer. The slide rack 300 has twelve slide positions 310 such that the slide rack 300 can hold twelve slides. The slides may be standard U.S. or international sized slides. The slide rack can be carried using the handles 330 on each end of the slide rack 300. FIG. 3b illustrates a front view of the slide rack 300.

Figure 3C:
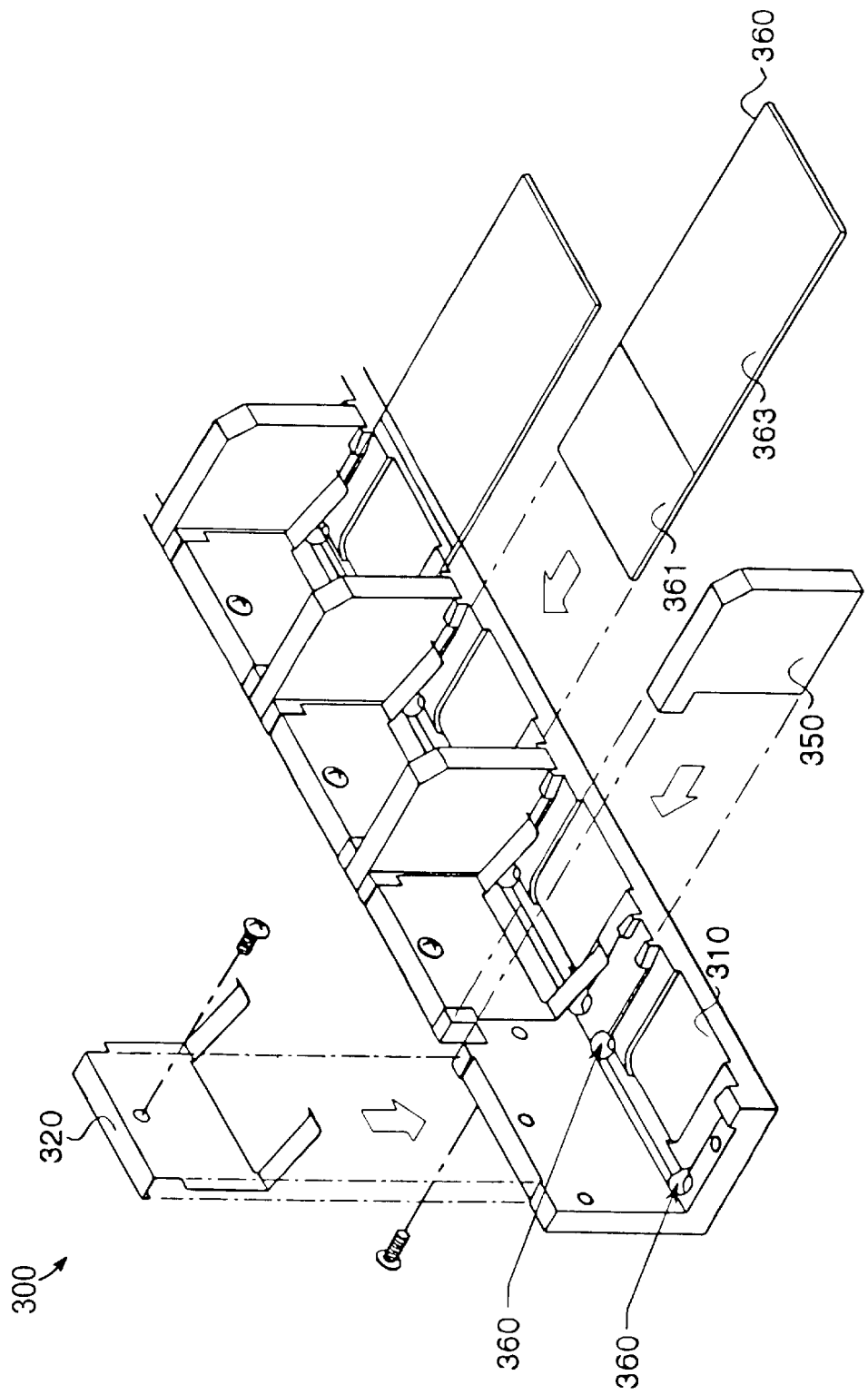
FIG. 3c illustrates a close-up perspective view of a slide rack for the autostainer.

FIG. 3c illustrates a close up view of four slide positions on a slide rack. Each position is shaped to accept a standard U.S. or an international sized slide 360. To hold the slide 360 in place, each slide position includes a stainless steel spring clip 320. The spring clip 320 is wide enough to accommodate common bar coding designations. The stainless steel spring clip 320 suspends the slide 360 by the frosted region 361 of the slide 360. Since the slide 360 is held only in the frosted region 361 of the slide, the slide rack 300 does not interfere with the specimen or any of the applied reagents. Specifically, since there is no contact with the specimen area (the nonfrosted area), there is no capillary effect, observed in prior art systems, that draws off the reagent. Each slide position 310 is separated from the next slide position by a divider 350. The divider 350 prevents reagent or buffer from one slide overflowing onto an adjacent slide. Each slide position 310 includes two drain holes 360 for draining excess buffer rinse solution that may reach the areas where the slide is clipped to the slide rack.

Z Head Assembly

Figure 4B:
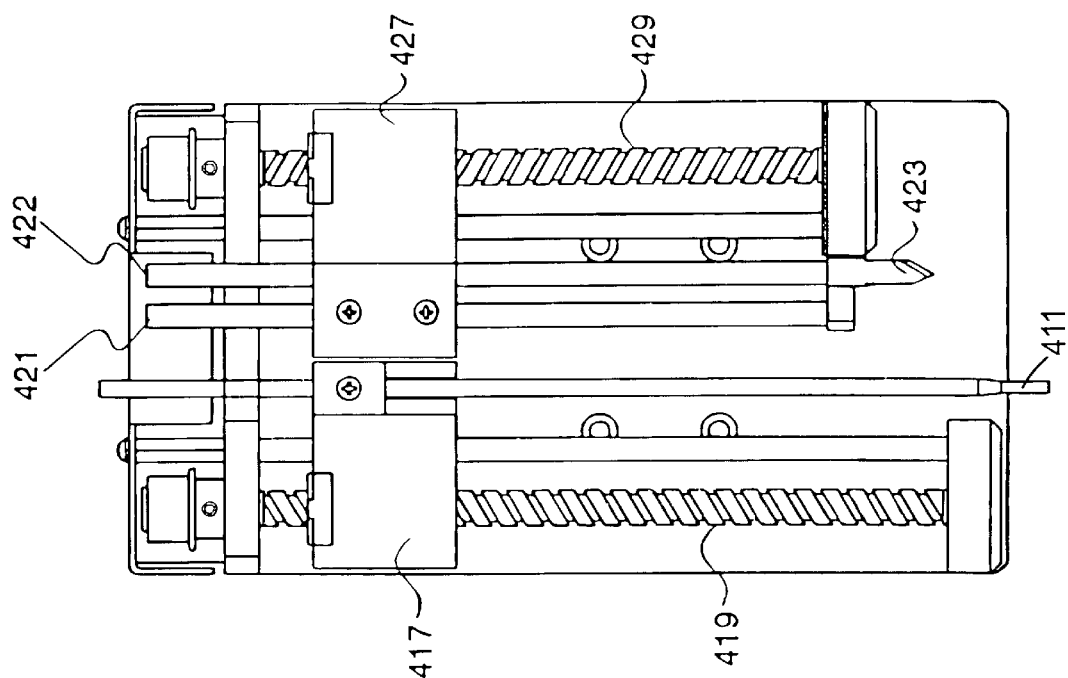
FIG. 4b illustrates a front view of the Z head assembly for the autostainer.
Figure 4A:
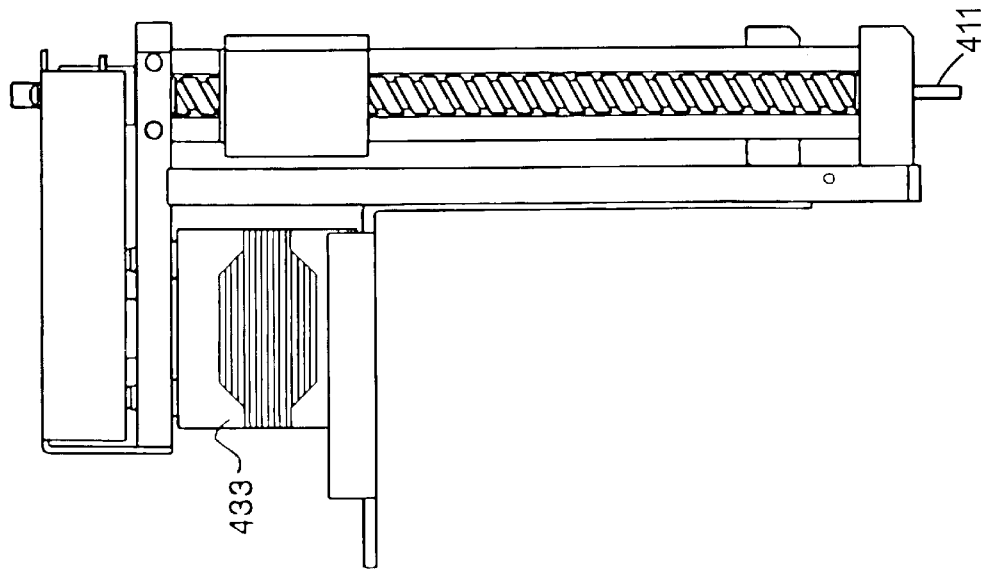
FIG. 4a illustrates a side view of the Z head assembly for the autostainer.

Referring back to FIG. 1b the autostainer 100 has a Z head assembly 135 that carries the buffer dispensing tube, the blow nozzle, and the reagent probe. FIGS. 4a and 4b illustrate a close-up of the Z head assembly. There are two different assemblies that move along the Z axis on the Z head: the reagent probe assembly and the air/buffer assembly.

The reagent probe assembly comprises the reagent probe 411, the reagent leadscrew nut block 417, and the reagent leadscrew 419. The reagent probe 411 is Teflon coated. The Teflon coating protects the stainless steel probe from corrosion and prevents reagent from sticking to the inside and outside walls of the probe. The reagent probe 411 includes custom circuitry that allows the reagent probe 411 to sense liquid levels. Since the reagent probe 411 can sense liquid levels, the probe goes into reagent vials only deep enough to obtain the desired amount of reagent. By only going deep enough to obtain the desired amount of reagent, the amount of contamination of the outside of reagent probe 411 is kept to a minimum. Furthermore, since the reagent probe 411 can sense liquid levels, it can determine if there is enough reagent in a vial to complete a staining run. This will be described in greater detail later.

The air/buffer assembly comprises the buffer tube 421, the air tube 422, the air nozzle 423, the air/buffer leadscrew nut block 427, and the air/buffer leadscrew 429. Since the reagent probe assembly and the air/buffer assembly are used independently, both assemblies can be driven by the same stepper motor driver 433. The entire Z Head assembly is constructed in a modular form such that it can be replaced as a single unit.

Autostainer Air Nozzle

Figure 5G:
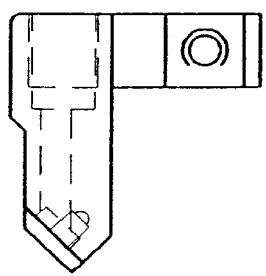
FIG. 5g illustrates a left side external view of the air nozzle with the nozzle lip in place.
Figure 5H:
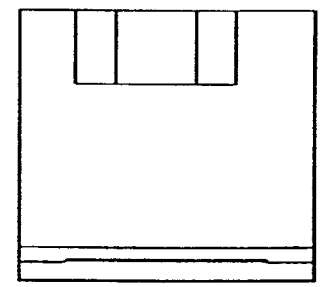
FIG. 5h illustrates a front view of the air nozzle.

The air nozzle on the Z head 135 (FIG. 1b) of the autostainer has been designed to uniformly distribute air across the surface of a glass slide such that an optimal amount of residual buffer solution remains to keep the specimen hydrated. This allows for accurate and consistent staining. FIGS. 5a through 5h illustrate the air nozzle. FIG. 5d illustrates a cut-away side view of the air nozzle. The air nozzle has an air shaft 511, a well 513, and a nozzle slit 521 (FIG. 5e). The nozzle slit forms a narrow opening when the nozzle lip 515 is coupled to the nozzle. The well 513 disperses the air such that uniform air flow is delivered out of the nozzle slit opening. The distribution angle of the nozzle allows the Z head to be narrower than prior art systems. Since the Z head is narrower, the slides can be grouped closer together such that the entire footprint of the autostainer has been reduced.

Autostainer Control and Programming

As stated in the previous section, the autostainer 100 is controlled by a personal computer system 190 (FIG. 1a). In one embodiment, the personal computer system 190 is a standard IBM compatible personal computer system running the Windows 95 operating system. The personal computer system 190 stores an autostainer control program 170 that is run when a user wishes to operate the autostainer 100.

The autostainer control program 170 is a sophisticated control program that implements many security, autoprogramming, control, and logging features. To fully describe the autostainer control program 170, this document will step through a sample use of the autostainer 100.

Autostainer Control Program Initialization

Figure 6:
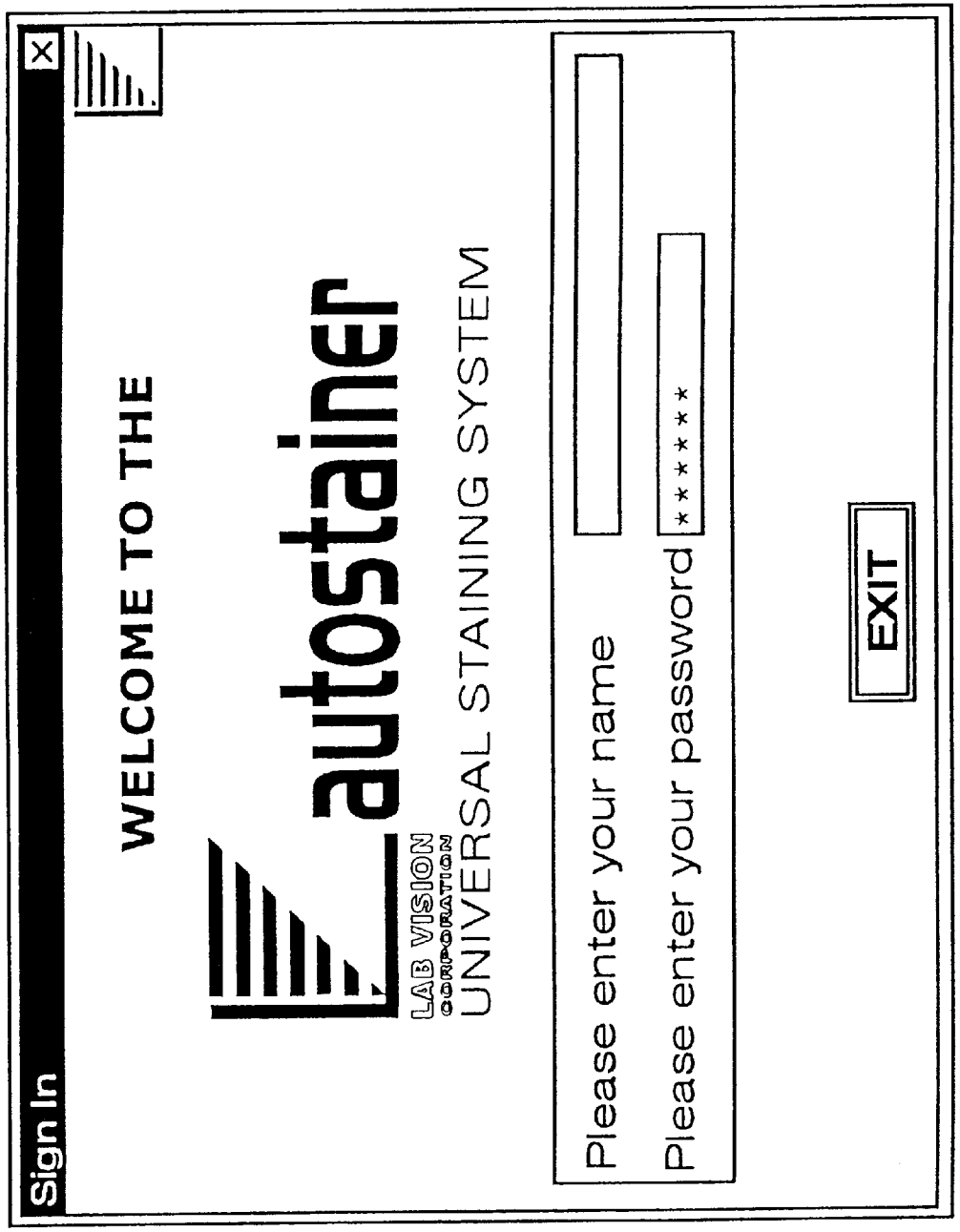
FIG. 6 illustrates the Sign-In Screen of the autostainer control program.
Figure 7:
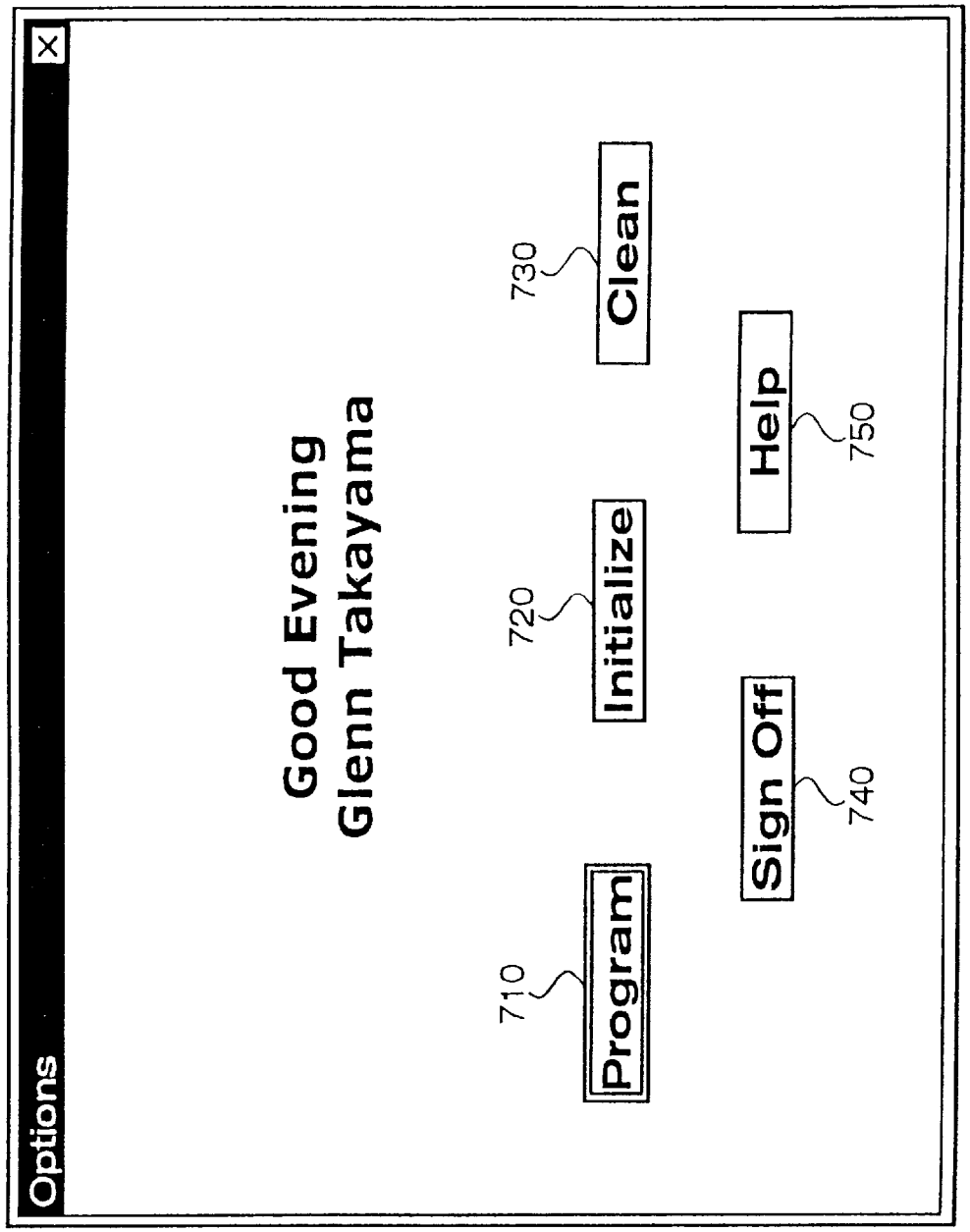
FIG. 7 illustrates the Options Screen of the autostainer control program.

When a user first runs the autostainer control program 170, a sign-in screen is displayed as illustrated in FIG. 6. The user enters a factory preloaded user name and password. After the factory preloaded user name and password have been entered, an option screen is displayed as illustrated in FIG. 7.

The option screen displays a set of functions that the user may select such as programming the autostainer for a run (Program 710), initializing the autostainer control program (Initialize 720), cleaning the autostainer (Clean 730), signing off (Sign Off 740), and displaying help information (Help 750). To initialize the autostainer control program 170, the user selects Initialize 720.

Figure 8:
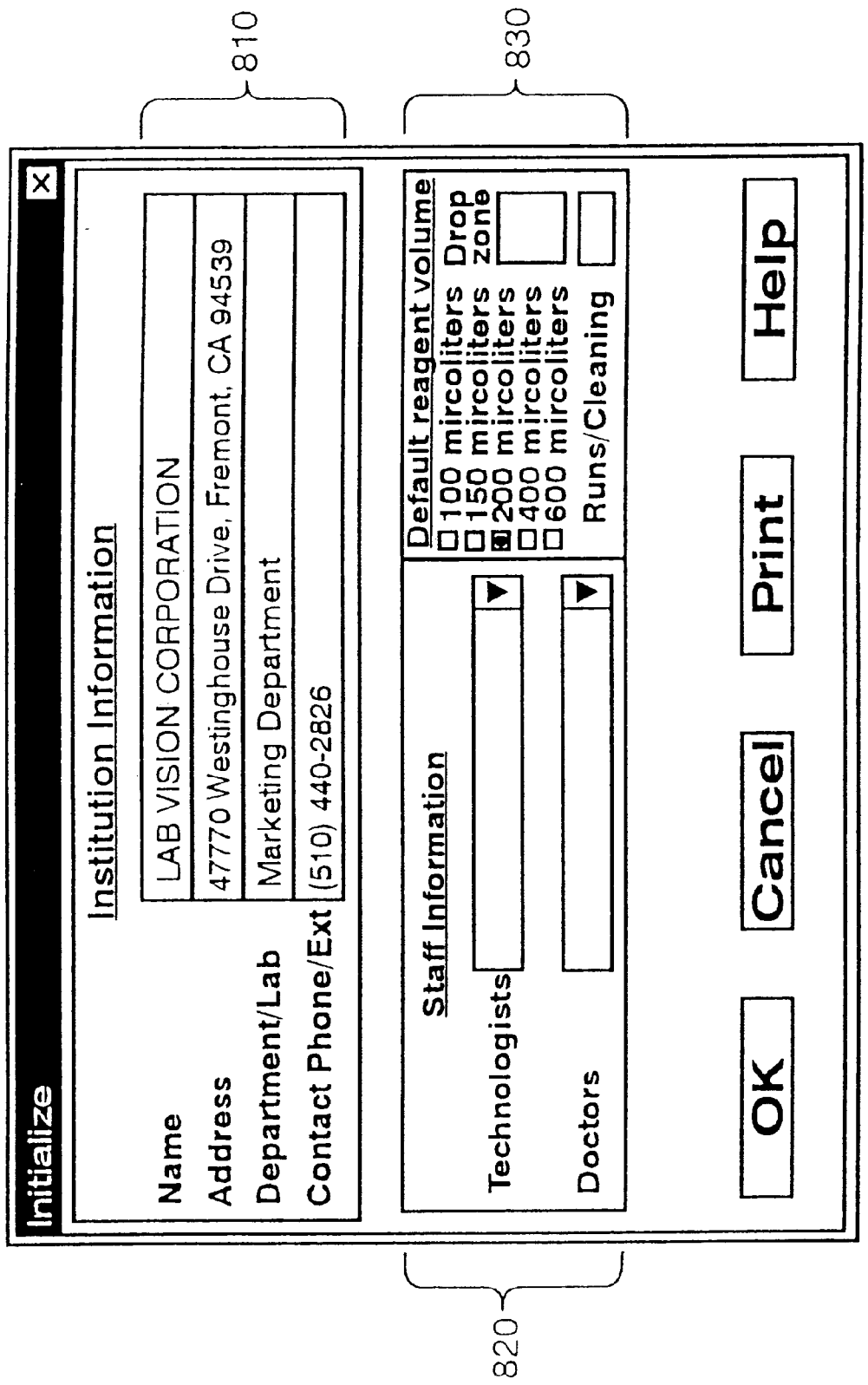
FIG. 8 illustrates the Initialize Screen of the autostainer control program.

After selecting the Initialize 720 button on the options screen, the Initialize screen is displayed as illustrated in FIG. 8. The initialization screen allows the user to enter information about the institution that will be using the autostainer in an institution information area 810. Below the institution information area 810 is a staff information area 820.

The staff information area 820 allows an entry to be created for each user that will use the autostainer 100. The staff information area 820 allows both doctors and technologists to be entered. Each user entry includes a user name, a user password, and a security level. The user name and password are used during the sign in process. The security level is used to limit access to features of the autostainer control program.

Finally, the Initialize screen allows a few autostainer operation parameters to be set. In the embodiment of FIG. 8, the parameter area 830 allows the user to specify the default reagent volume amount, the default reagent drop zone, and the number of runs allowed between cleanings.

The default reagent volume specifies the amount of reagent that will be used for all steps in any staining protocol. However, the default reagent volume can be overridden by specifically programming a different amount, as will be described later. The default reagent drop zone specifies the default location where reagent will be applied to the slides. The default reagent drop zone can be overridden on the Slide Layout Map screen of FIGS. 19 and 20, as will be described later.

The number of slides allowed between cleanings specifies how many times the autostainer may be used between maintenance cleanings. When the specified number of slides have been treated, a user will be notified that a cleaning cycle should be run at the Options screen.

Creating a Staining Run

To run the autostainer, a user signs in with his or her user name and password, as previously described with reference to FIG. 6. Then, at the Option screen displayed in FIG. 7, the user selects the Program button 710. After the selecting the Program button 710, a blank Program Staining Run screen is displayed as illustrated in FIG. 9a.

The Program Staining Run screen is the central screen used to program a staining run. The Program Staining Run screen displays a grid of the steps that will be performed on each slide. The rows of the grid list the slides that will be stained. The columns of each row in the grid contain the patient name and case number, the doctor name, and all the steps that will be performed on that slide (row). The list of steps that will be performed on a slide, or groups of slides, are referred to as a "protocol."

Several pull-down menus are available on the top of the program staining run screen, including "File" and "Edit." The File pull-down menu allows the user to create a new staining run program, open an old staining run program, save the current staining run program, and print the current staining run program. The Edit pull-down menu displays a list of all the available reagent categories that can be edited. To edit a reagent, the user selects the reagent category from the Edit pull-down menu and then an appropriate Edit reagent list screen will be displayed. The editing of reagents will be explained later. The Edit pull down menu also lists a "Detection Kit" item. If the Detection Kit item is selected, then the Detection Kit Lot maintenance screen is displayed. The Detection Kit Lot Maintenance screen allows detection kits consisting of two or more reagents to be created.

Also available at the top of the program staining run screen is a "Copy" function. One or more steps in a protocol can be selected using the cursor control device, and then the "Copy" function can be used to copy the steps. The user can then move the cursor to another slide row and "Paste" the steps into that slide's protocol. Thus, by cutting and pasting similar steps, the programming time is decreased.

Beneath the grid of slide and protocol information are six buttons for accessing additional programming features. The slide information button 910 moves the user to a Slide Information screen in order to enter new or edit existing patient information. The Protocol Template button 920 moves the user to a Protocol Template Design screen, where a new staining protocol template can be created or a stored protocol template retrieved. The Next button 930 is selected when the user is satisfied with the information in the Program Staining Run screen and wishes to start the staining run. The Print button 940 request the user to indicate if he or she wants a hard copy printout of the programmed staining grid that is currently displayed, or an immunohistochemical report (IHC), as illustrated in FIG. 9b. The user simply selects the hard copy that is desired. The Exit button 950 returns the user to the Option screen as illustrated in FIG. 7. If the program has been changed, the user is presented with the option of saving the program. The Help 960 button displays context sensitive help information.

The general procedure for programming a staining run is as follows: (1) enter the slide information for each slide; (2) select an existing or create a new protocol for staining run; (3) select the reagents that will be used in the staining run; and (4) load the slides and reagents and start the run. Each step merits its own discussion.

1) Entering Slide Information

To enter patient information for a staining run, the user selects the Slide Information button 910 from the Program Staining Run screen of FIG. 9a. This moves the user to the Slide Information screen, as illustrated in FIG. 10.

The Slide Information screen has input areas to allow the user to enter a patient name, a patient case number, the number of slides for that patient, and the doctor that requested the slides. After entering this information for a first patient, the form is cleared and the user can enter information for a next patient. The four buttons on the bottom of the Patient Information screen are used to perform various operations.

The Delete button 1020 is used to delete a patient entry or case entries. The user can delete a patient entry using the patient selector arrow 1011 to select a particular patient name, and then click on the Delete button 1020 to delete the selected patient entry. The user can delete a particular case for a patient entry using the patient selector arrow 1011 to select a particular patient name, then using the case selector arrow 1081 to select a particular case number, and then click on the Delete button 1020 to delete the selected case.

The Cancel button 1030 allows the user to cancel all the entered patient information. When a user selects the Cancel button 1030, the user returns to the Program Staining Run screen and none of the entered patient information is saved.

The Help button 1040 can be selected to receive context sensitive help information. Thus, the Help button 1040 displays help information about the Slide Information Screen.

After entering all the desired patients, the user selects the Finish Entry button 1010 to return to the Program Staining Run screen with the new patient information displayed. After entering all the patient information, the next step is to select an existing or create a new protocol for staining run. Thus, from the Program Staining Run screen the user selects the Protocol Template button 920 (FIG. 9a).

2) Creating A New Or Accessing An Existing Protocol Template

To select a protocol template for a staining run, the user selects the Protocol Template button 920 from the Program Staining Run screen. This moves the user to the Protocol Template Design screen as illustrated in FIG. 11.

Figure 11:
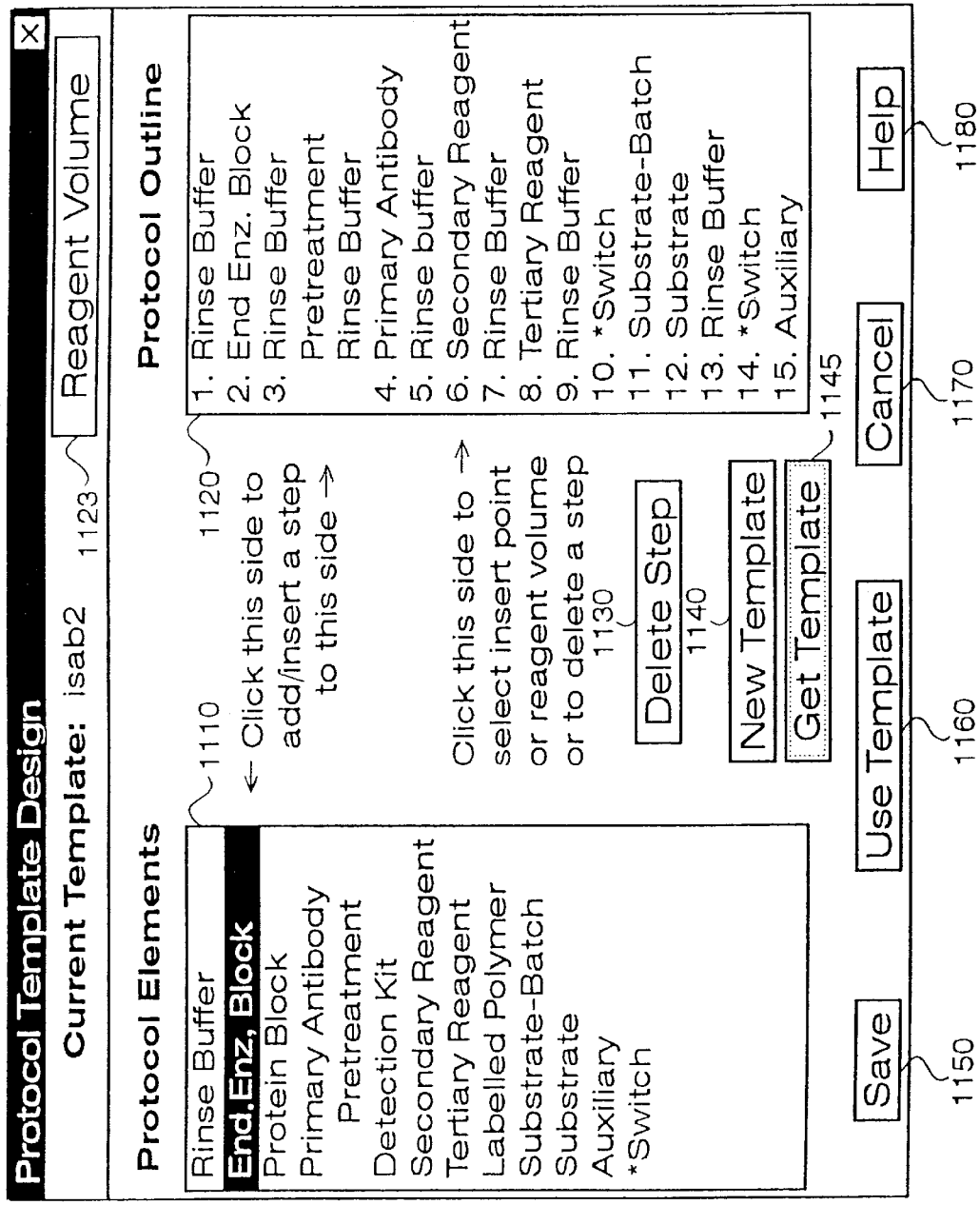
FIG. 11 illustrates the Protocol Template Design Screen of the autostainer control program.

The Protocol Template Design screen of FIG. 11 is divided into two vertical columns. The left column is the Protocol Elements column 1110. The Protocol Elements column 1110 lists the various steps that can be used to create a protocol. The right column is the Protocol Outline column 1120. The Protocol Outline column 1120 lists the steps that have been selected for the current protocol.

The Protocol Template Design screen enables the user to create staining protocol templates to be used in the staining runs. Protocol templates can be created and stored for future use. To create a protocol template, the user selects protocol steps from the Protocol Elements column 1110 and moves them to the Protocol Outline column 1120.

The available protocol steps include: Endogenous Enzyme Block, Protein Block, Primary Antibody (and Pretreatment), Detection Kit, Secondary Reagent, Tertiary Reagent, Labeled Polymer, Substrate-Batch, Substrate, Auxiliary, Switch, and Rinse Buffer. The specific reagents used during reagent steps are assigned to each slide from the Program Staining Run screen, as will be described in the next section.

Referring to FIG. 11, the Rinse Buffer protocol element or step should be programmed between all protocol template steps to remove reagents from the slides between the staining run steps. The default Rinse Buffer step can be replaced by a blow step by clicking on the Rinse Buffer step droplet icon on the Program Staining Run screen (FIG. 9b) with the right mouse button. This replaces the droplet icon with a wind icon, indicating a blow step.

The Substrate-Batch Protocol step allows the use of unstable substrates that need to be prepared immediately prior to application. The Substrate-Batch Protocol step splits the staining run into two phases: a first phase prior to the application of the unstable substrate, and a second phase batching all the steps starting with the unstable substrate application. The autostainer will stop after all the steps in the first phase and beep to indicate that the substrate should be prepared. The user then prepares the substrate and loads it into a designated position in the reagent rack. After the user has placed the unstable substrate into the designated position in the reagent rack, the user prompts the autostainer to continue the staining run.

The Switch step allows a user to indicate the switching of waste from one container to another. The Switch step is primarily used to separate hazardous waste from nonhazardous waste. A protocol template containing a Switch step switches from the primary (nonhazardous) waste system to a secondary (hazardous) waste system. On the Program Staining Run screen, the first Switch step will be displayed as a skull and crossbones to indicate a switch to the secondary (hazardous) waste system. The next Switch step will be displayed as a flower icon to indicate a switch to the primary (nonhazardous) waste system. Accordingly, subsequent switch steps alternate between the secondary (hazardous) waste system and the primary (nonhazardous) waste system. Switch steps must always be preceded by a rinse step.

As illustrated in FIG. 11, the Protocol Template Design screen has the following function buttons: New Template 1140, Get Template 1145, Use Template 1160, Delete 1130, Reagent Volume 1123, Save 1150, Cancel 1170, and Help 1180. The New Template 1140 button clears the Protocol Outline column 1120 such that a new template may be created. The Get Template 1145 button displays a file requester box such that an existing template may be fetched. The Use Template 1160 button installs the protocol template displayed in the Protocol Outline column 1120 and returns to the Program Staining Run screen. Delete 1130 deletes a highlighted step from the Protocol Outline column 1120. The Reagent Volume 1123 button assigns a reagent dispense volume to a highlighted step (or all the steps if a specific step is not highlighted) in the Protocol Outline column 1120. The Save 1150 button saves the protocol template currently displayed in the Protocol Outline column 1120 into a file. The Cancel button 1170 allows the user to cancel all the entered information and returns the user to the Program Staining Run screen. The Help button 1180 can display context sensitive help information.

After selecting the Save 1150 button, the Use Template 1160 button, or the Cancel button 1170, the user is returned to the Program Staining Run screen.

3) Selecting Reagents Used in the Staining Run

When the user returns to the Program Staining Run screen (FIG. 9b) after selecting a protocol template, the first reagent step to be programmed will be flashing. There are two different ways of assigning reagents to the slides. The first method is to edit the reagents for a slide by selecting the slide. The second method is to select a reagent box on the Program Staining Run screen and an appropriate reagent list will be displayed such that a reagent may be selected.

Figure 12:
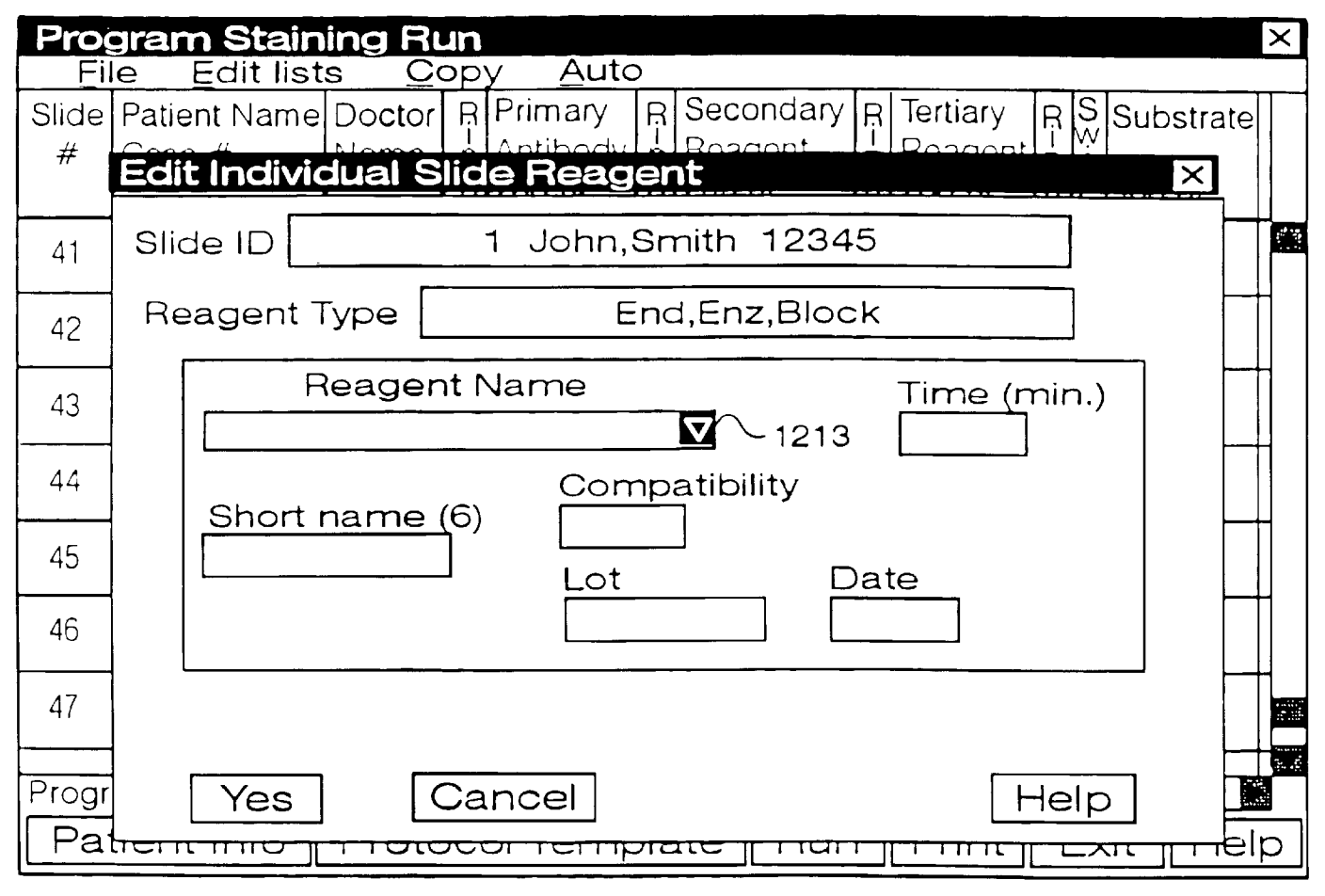
Figure 13:
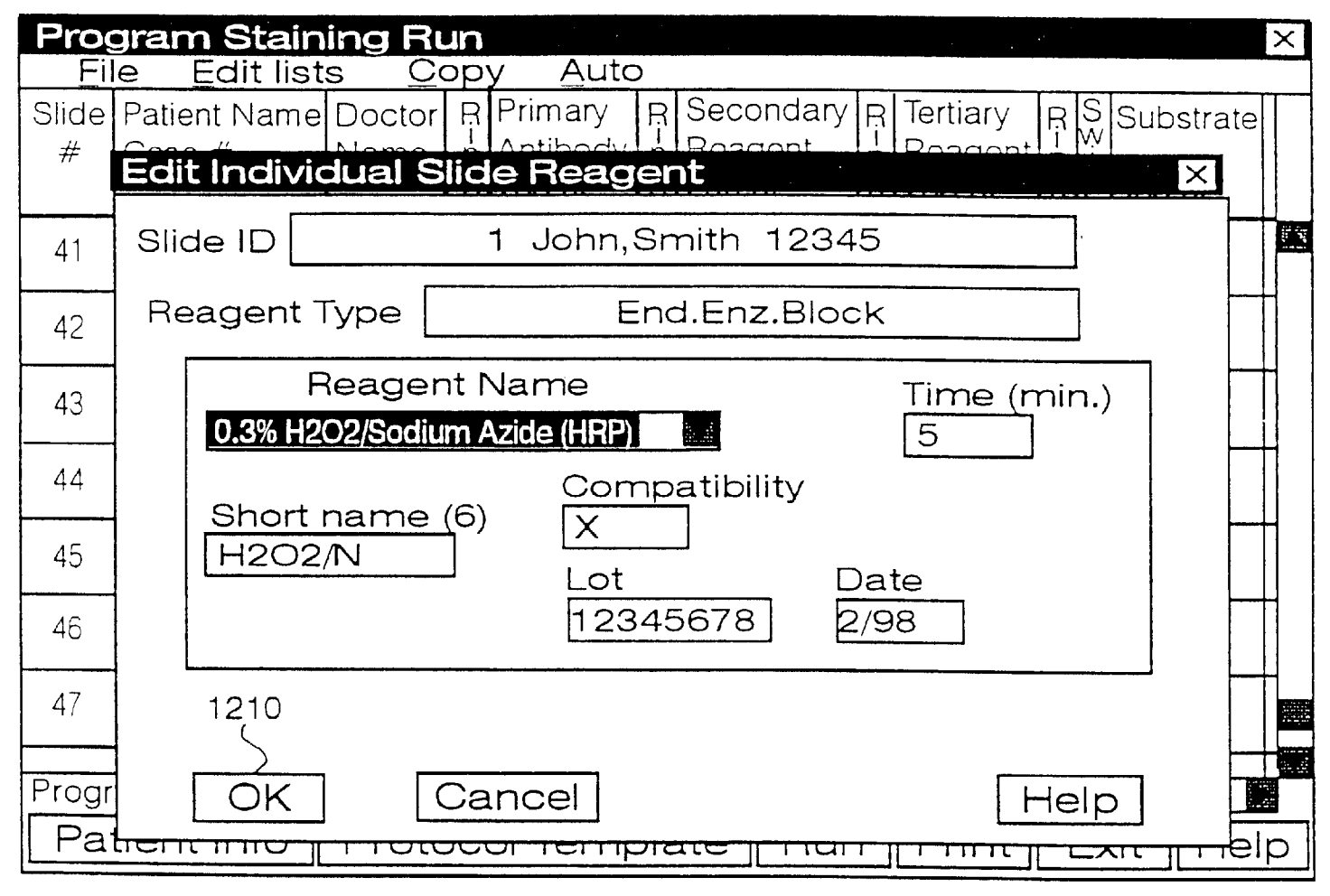

As shown in FIG. 12, to edit an individual slide, a user can select a slide tile and then click on the "Edit Lists" item displayed at the top of the reagent list. This brings up the Edit Individual Slide Reagent Window. For example, FIG. 12 illustrates the Edit Individual Slide Reagent Window for the Endogenous Enzyme Block of Slide 1. To select a reagent, the user can use the down arrow 1213 in the reagent name field to select the desired reagent. FIG. 13 illustrates how the Edit Individual Slide Reagent Window appears after the $H_2O_2/N$ reagent has been selected.

Figure 14:
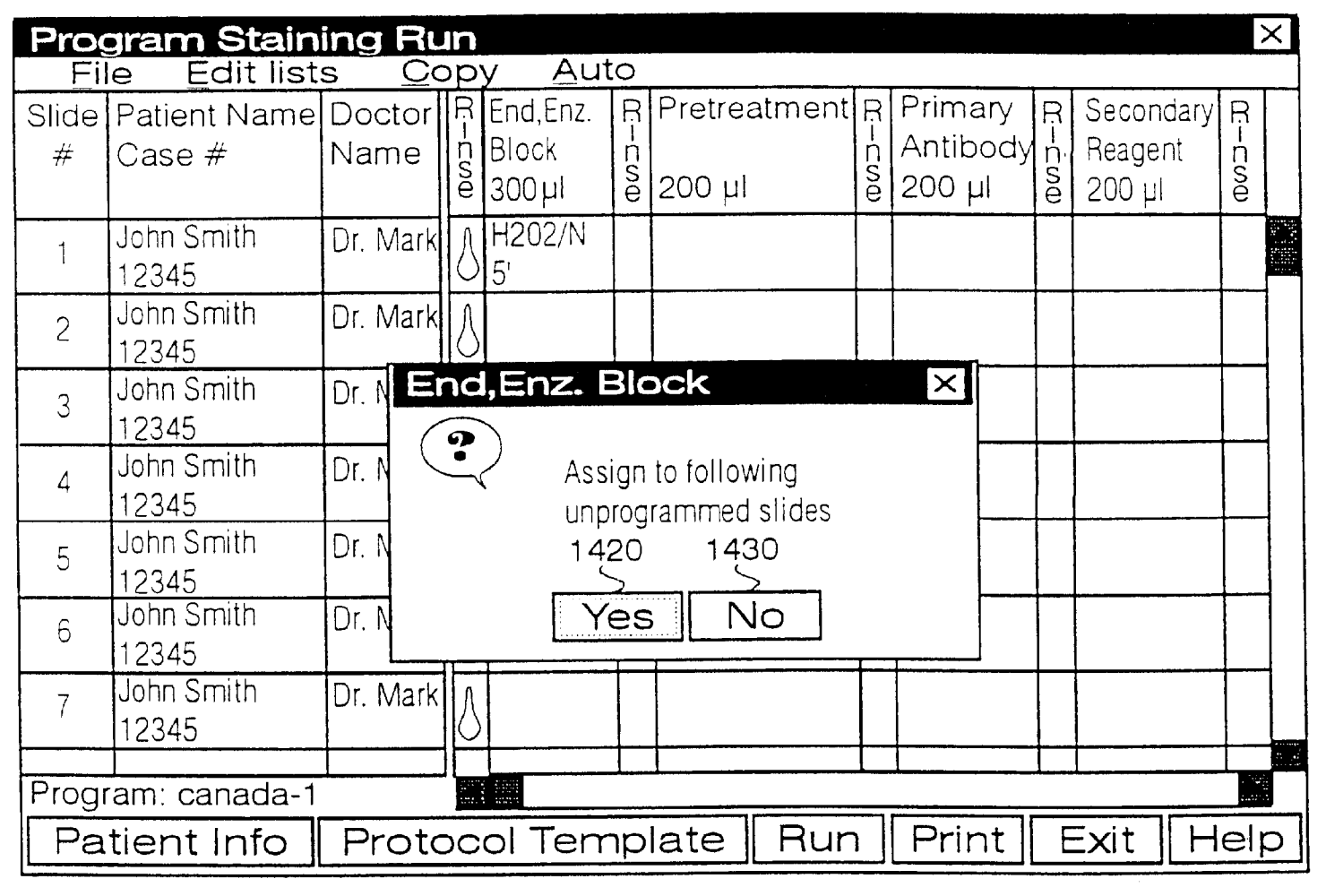

Using the Edit Individual Slide Reagent Window, slide specific edits can be made. No edits made on the Edit Individual Slide Reagent Window will affect the reagent file. However, after the user selects the "OK" button 1210, the user will be asked if he or she wants the same reagent applied to all the unprogrammed slides, as illustrated in FIG. 14. If all or most of the slides are undergoing the same treatment, the user should select the "yes" button 1420 such that the autostainer program fills in the selected reagent for the same step in the remaining unprogrammed slides. If the majority of the slides have different protocols, the user should select the "no" button 1430. The remainder of the reagents for the slide can be edited in the same manner.

Figure 15:
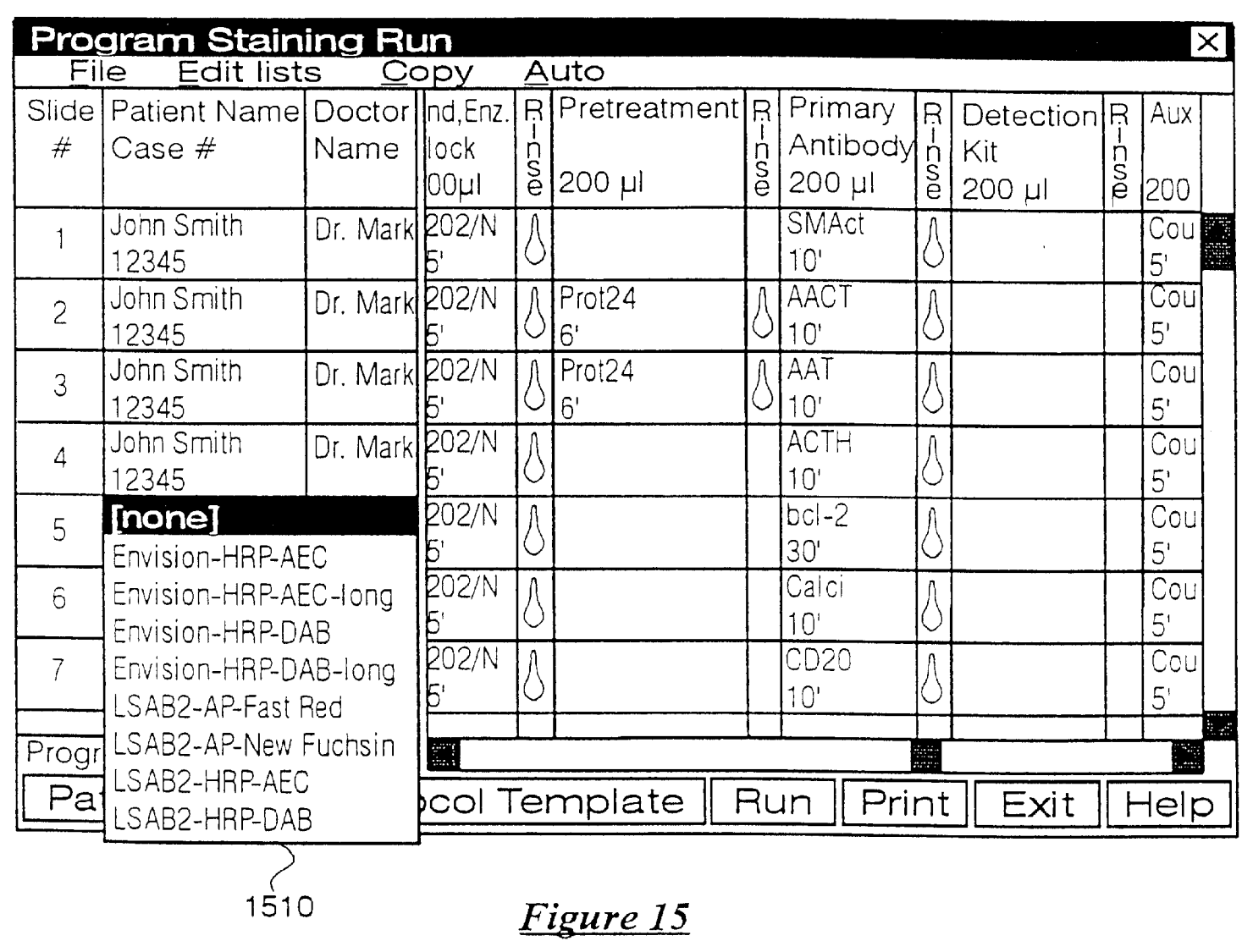

The other method of editing reagents is to select a particular reagent tile from the Program Staining Run screen grid. This will bring up an appropriate list of reagents that may be selected. For example, FIG. 15 illustrates a Detection Kit tile for slide 3 highlighted such that an appropriate list of Detection Kits is displayed in a pop-up window 1510. The user simply selects the desired Detection Kit from the pop-up window 1510. Note that one of the Detection Kits in the list is "None" so the tile may be cleared. After selecting a reagent, a window will ask the user if the same reagent should be assigned to the remaining unprogrammed slides, as explained above.

The user programs all of the reagent steps using the two methods described above. To reduce the work involved, the user can use the "Copy" command from the menu to copy protocol and reagent information from slides that have already been programmed into unprogrammed slide rows.

The autostainer of the present invention includes a compatibility check feature to prevent incompatible reagents from being used on the same slide. In a present embodiment there are two compatibility tests performed, although more can be added in future versions. The first compatibility check tests the species reactivity compatibility of the primary antibody and the secondary reagent used. The second compatibility check tests the compatibility rules dictated by the enzyme used in the detection system. The following chart summarizes the current compatibility rules:

Species Reactivity Compatibility Rules
First Compatibility Check: Species Compatibility

| Reagent Type | Description | Compatibility Code |
| --- | --- | --- |
| Primary Antibody | All monoclonal primary antibodies raised in mouse (e.g., mouse anti-human) | A |
| Primary Antibody | All polyclonal primary antibodies raised in rabbit (e.g., rabbit anti-mouse IgG) | B |
| Secondary Reagent | All secondary reagents (antibodies) compatible with monoclonal antibodies raised in mouse (e.g., biotinylated antimouse IgG) | A |
| Secondary Reagent | All secondary reagents (antibodies) reacting with polyclonal antibodies raised in rabbit (e.g., biotinylated antirabbit IgG) | B |

Second Compatibility Check: Enzyme System Compatibility

| Reagent Type | Description | Compatibility Code |
| --- | --- | --- |
| Endogenous Enzyme Block | HRP-compatible | X |
| Endogenous Enzyme Block | AP-compatible | Y |
| Tertiary Reagent | HRP-labeled streptavidin | X |
| Tertiary Reagent | AP-labeled streptavidin | Y |
| Substrate | HRP-compatible substrates (i.e. DAB, AEC) | X |
| Substrate | AP-compatible substrates (i.e. Fast Red, New Fuchsin) | Y |

When a user attempts to enter a reagent that is incompatible with a previously selected reagent, the Incompatible Reagent Warning Box is displayed, as illustrated in FIG. 16. The Incompatible Reagent Warning Box asks the user if the incompatible reagent should be used. If the user selects "no" then an incompatible reagent is erased. If the user selects "yes", then the incompatible reagent remains.

Figure 17:
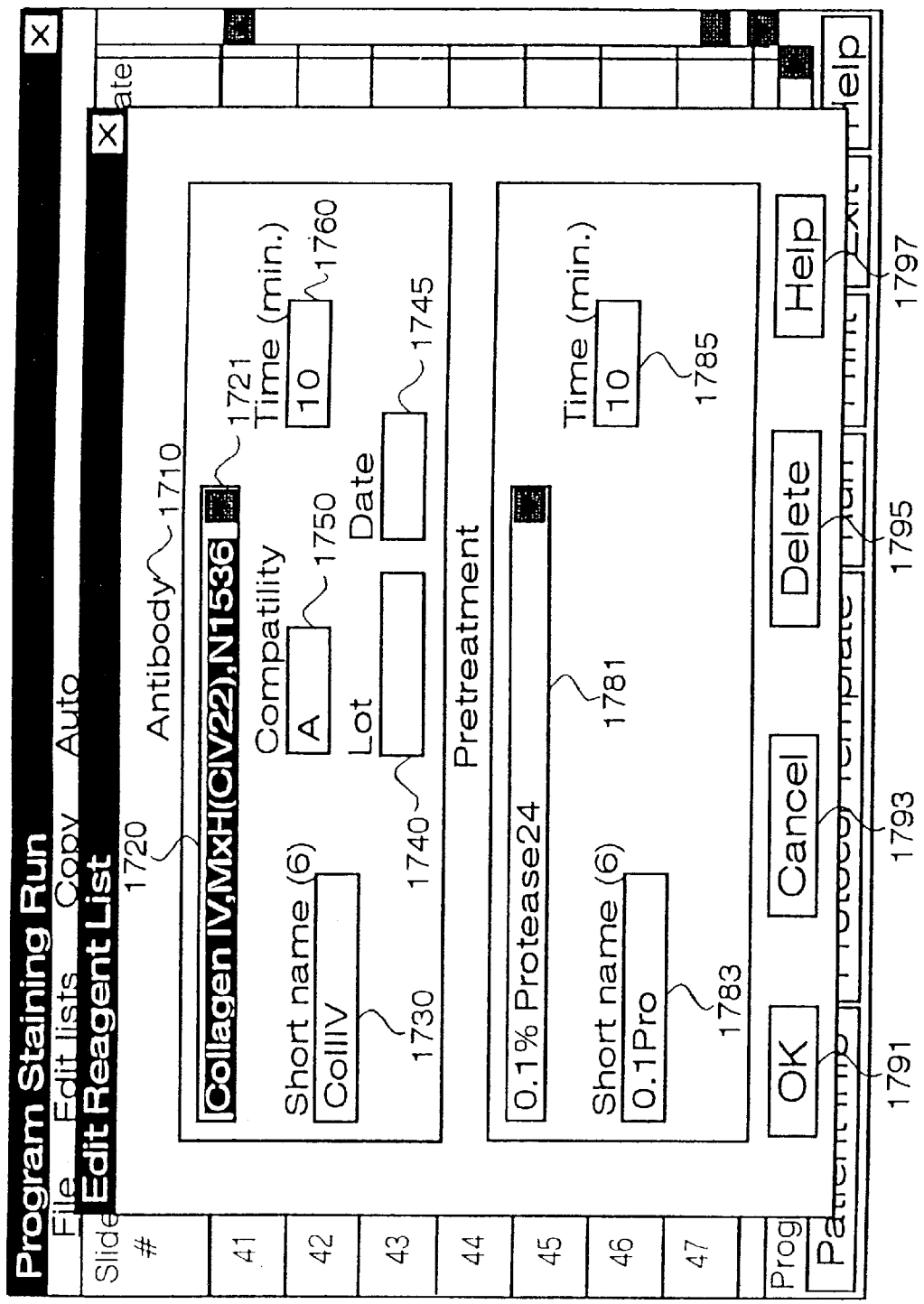
FIG. 17 illustrates the Edit Reagent List Screen of the autostainer control program.

To edit the actual reagents that are available for use, the user selects a reagent type from the Edit pull-down menu on the Program Staining Run screen. The Edit Lists pull-down menu displays the following reagents that can have their parameters modified: Endogenous Enzyme Block, Protein Block, Primary Antibody, Pretreatment, Secondary Reagent, Tertiary Reagent, Labeled Polymer, Substrate, and Auxiliary. When the reagent type is selected, such as the Primary Antibody reagent, the user is moved to the Edit Reagent List screen, as illustrated in FIG. 17.

At the top of the Edit Reagent List screen is a title 1710 that lists the type of reagent that can be displayed. In the example of FIG. 17, the Collagen IV antibody of the Primary Antibody type of reagent is displayed. The remainder of the Edit Reagent List screen displays the relevant information for the particular reagent that is on the screen. The information includes: the reagent long name 1720, the reagent short (10 character) name 1730, a lot number 1740, an expiration date 1745, a compatibility code 1750, and an incubation time 1760. To edit the information, the user simply types in the desired field. In the particular case of the Primary Antibody reagent, the information about the corresponding pretreatment is also displayed including the pretreatment name 1781, the pretreatment short (10 character) name 1783, and the incubation time 1785. The information about the corresponding pretreatment can also be edited by typing in the desired field.

To select a different reagent of the type of reagent listed in the title 1710, the user uses the name selector arrow 1721 or moves the cursor to the reagent long name field and presses the down arrow key until the desired reagent is displayed. The user then hits Enter to obtain the information about that particular reagent. To delete the reagent that is currently displayed, the user can select the Delete button 1795 at the bottom of the screen.

To return to the Program Staining Run screen, the user selects the OK button 1791. To return to the Program Staining Run screen without saving the changes that have been entered the user can select the Cancel button 1793. Context sensitive help is available by pressing the Help button 1797.

4) Loading Reagents Used in the Staining Run

Once all the patient information has been entered, the desired slide protocols have been set up, and the desired reagents have been selected, the autostainer is ready to be operated. Thus, the user must physically load the slides and reagents. These steps will be described in the next section.

Autostainer Operation

Figure 19:
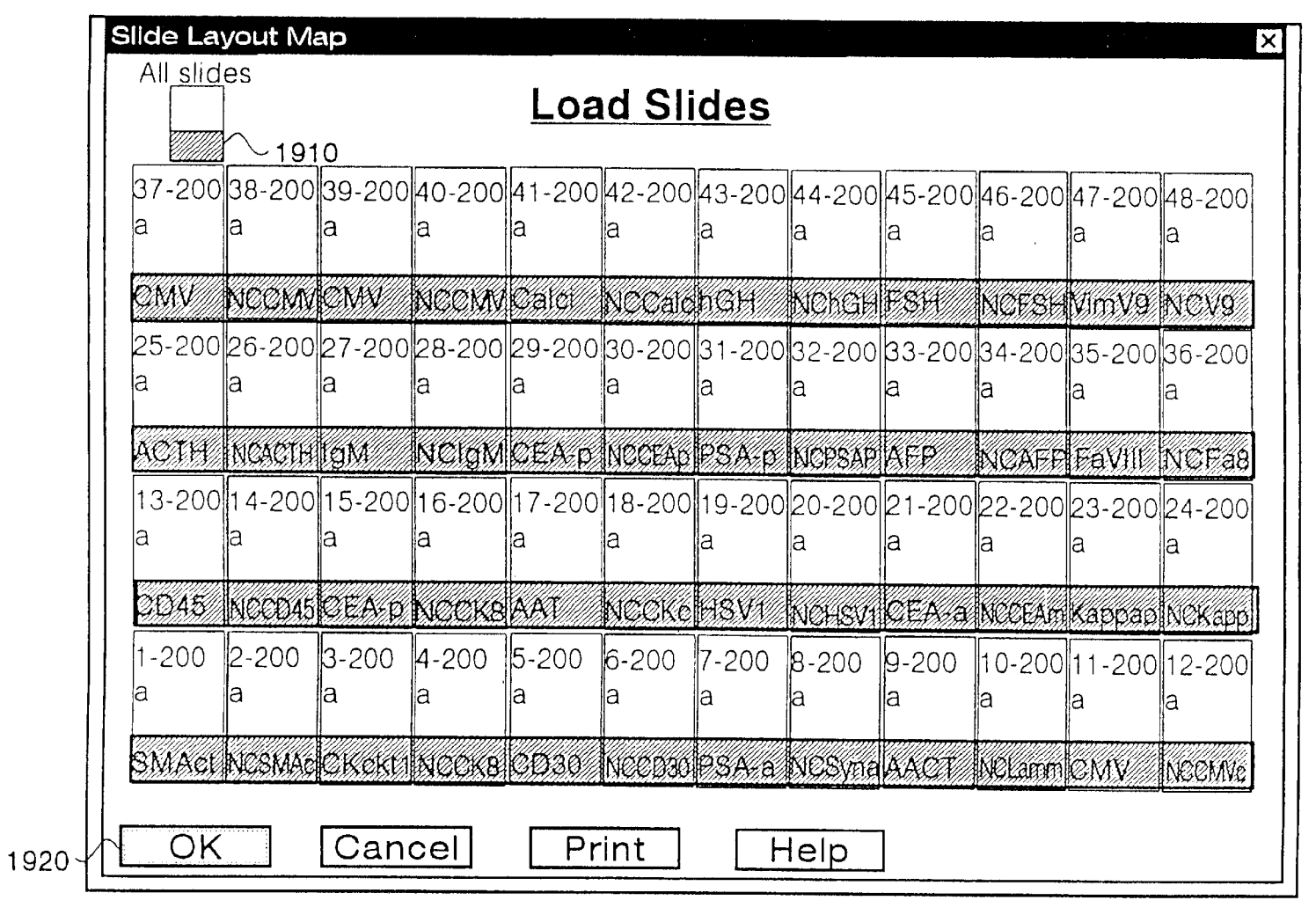

After the patient information, the slide protocols, and the desired reagents have been entered, the Program Staining Run screen grid will appear as it does in FIG. 18. To begin the staining operation, the user selects the Run button at the bottom of the Program Staining Run screen. The autostainer program will ask the user if the staining run program should be saved, as illustrated in FIG. 18. After saving (or not saving) the programmed information, the user is moved to the Slide Layout Map screen, as illustrated in FIG. 19.

The Slide Layout Map screen displays a grid of all 48 slides. Each slide is identified with the slide number, the primary antibody abbreviation, the primary antibody volume, and the case number.

Figure 20:
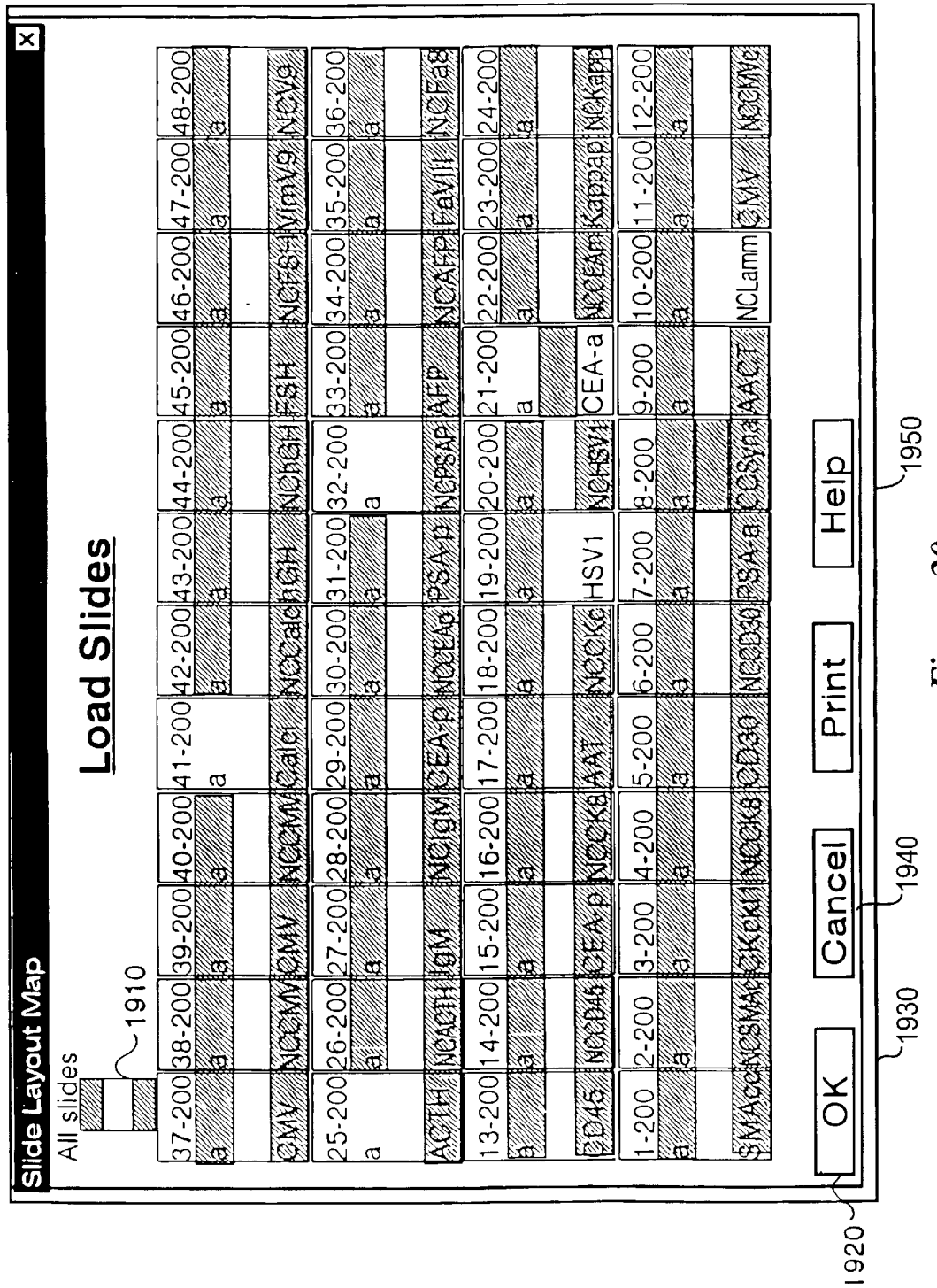
FIG. 20 illustrates the Slide Layout Map Screen of the autostainer control program.

Each slide also has a designation of where the reagent will be dispensed onto the slide. The non-frosted zone of each slide is divided into three dispense zones. The default dispense location is set on the Initialization screen of FIG. 8. To change the dispense location for all the slides, the user can select any of the three zones on an "All Slides" icon 1910 in the upper left-hand corner. By toggling a zone of the "All Slides" icon 1910, all the slides on the Slide Layout Map screen are affected. Furthermore, the dispense location for individual slides can be set by toggling the three sections of the individual slide representation. FIG. 20 illustrates the Slide Layout Map screen after the top third of the "All Slides" icon 1910 has been toggled and several individual slides have been toggled.

The Slide Layout Map screen allows the user to make a final check of the staining run. If the user is not satisfied, the user can select the Cancel button 1930 to return to the Program Staining Run screen. The user can select the Print button 1940 to print the Slide Layout Map screen. The Help button 1950 displays context sensitive help information.

If the user is satisfied with the contents of the Slide Layout Map screen, then the user must load the slides into the autostainer as specified on the Slide Layout Map. After the user has loaded the slides, the user selects the OK button 1920 to proceed. After the user selects the OK button 1920 on the Slide Layout Map screen, the autostainer control program proceeds to calculate the most efficient dispensing pattern for performing the desired slide protocols.

Figure 21:
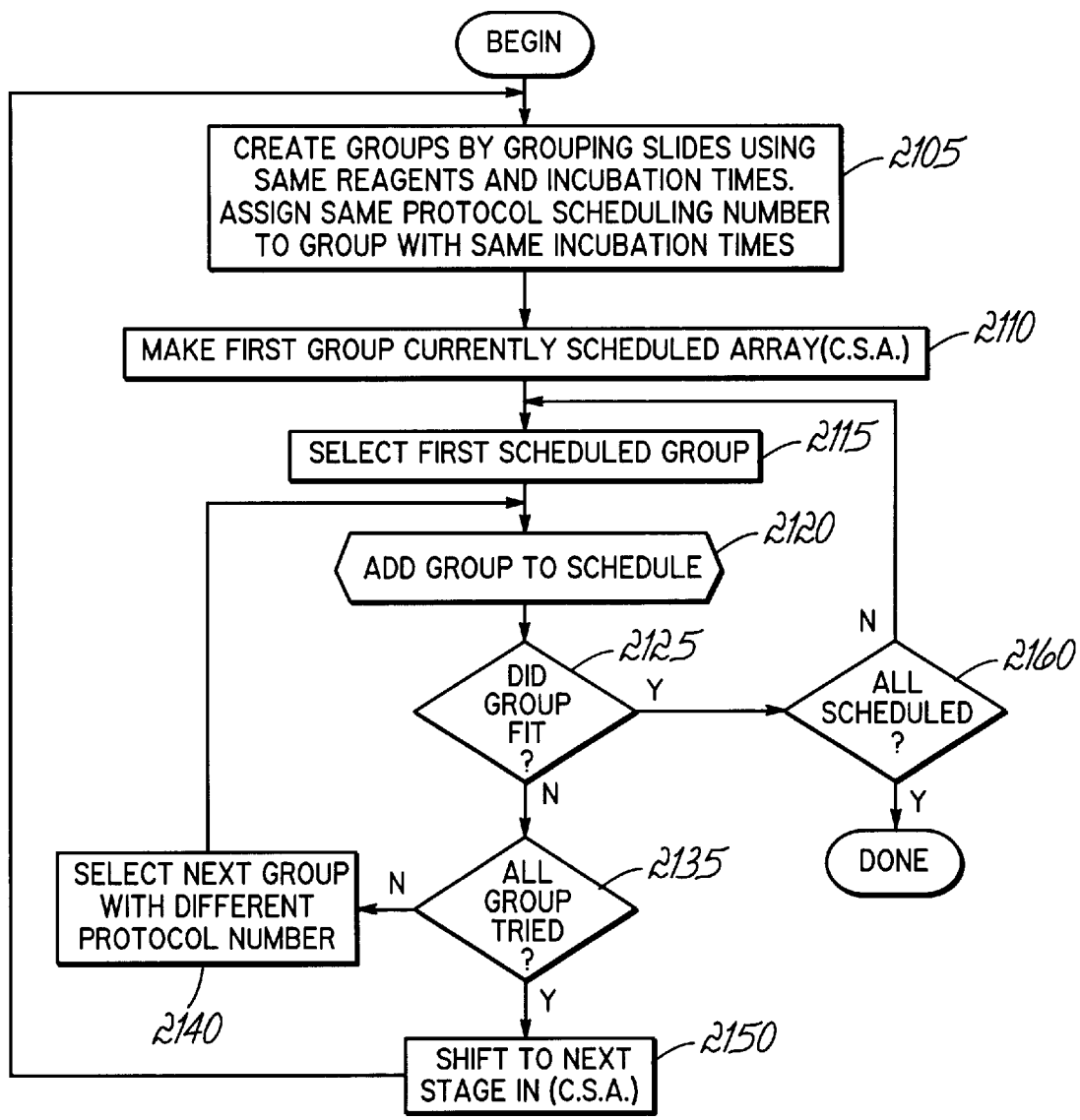
FIG. 21 illustrates a summary of the scheduling system of the autostainer control program.
Figure 22A:
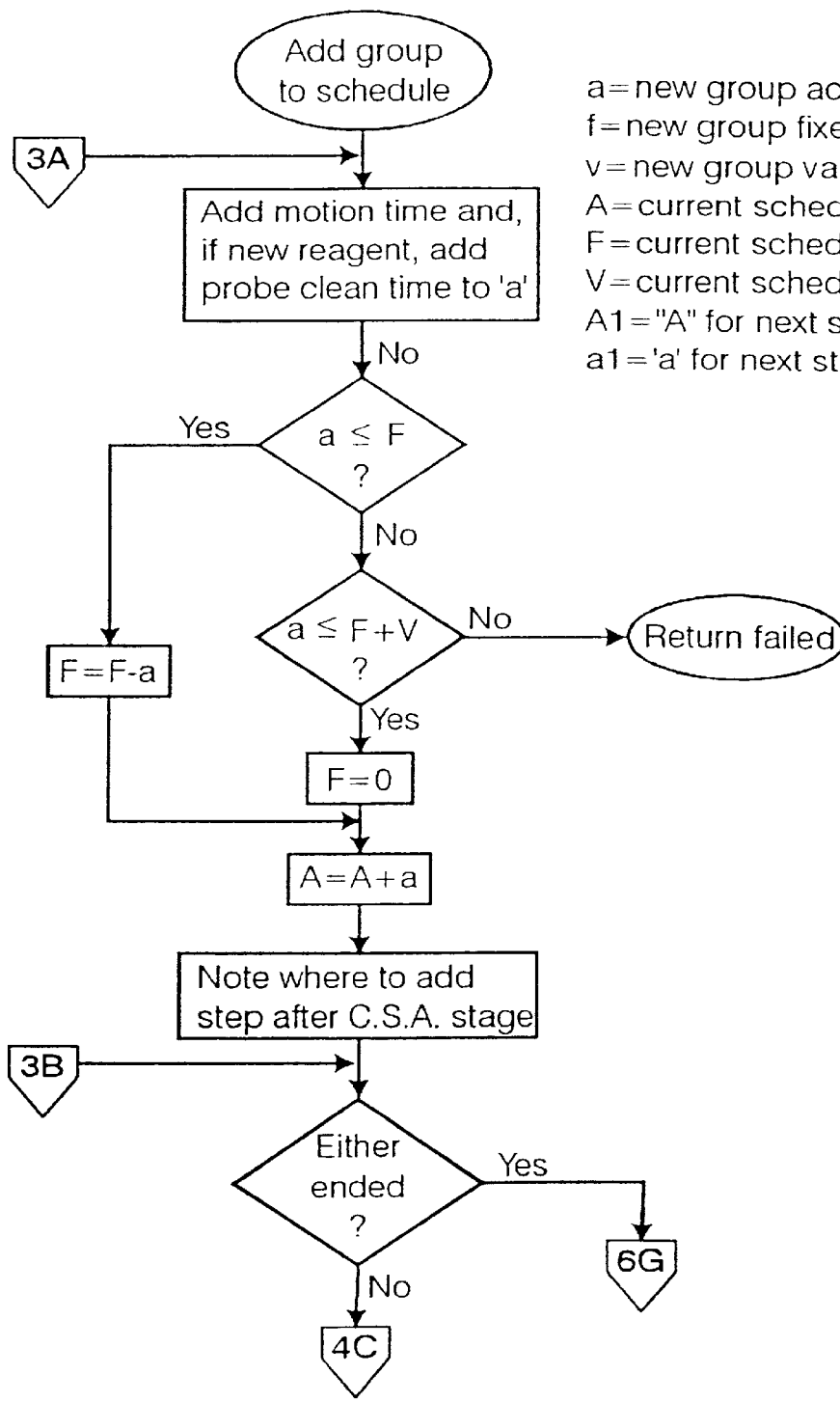
FIGS. 22a through 22d list the details of adding a new group to the Currently Scheduled Array.
Figure 22B:
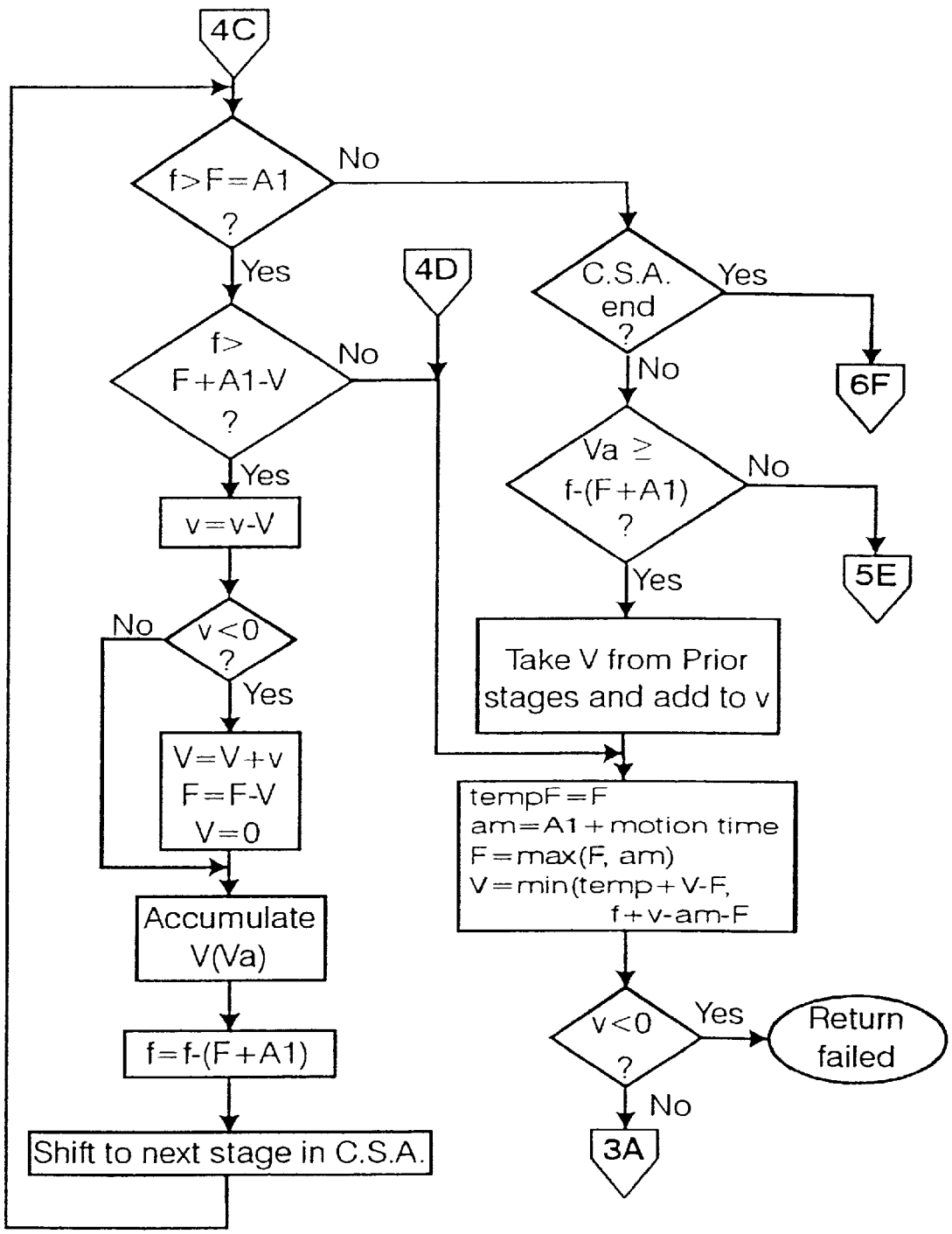
Figure 22C:
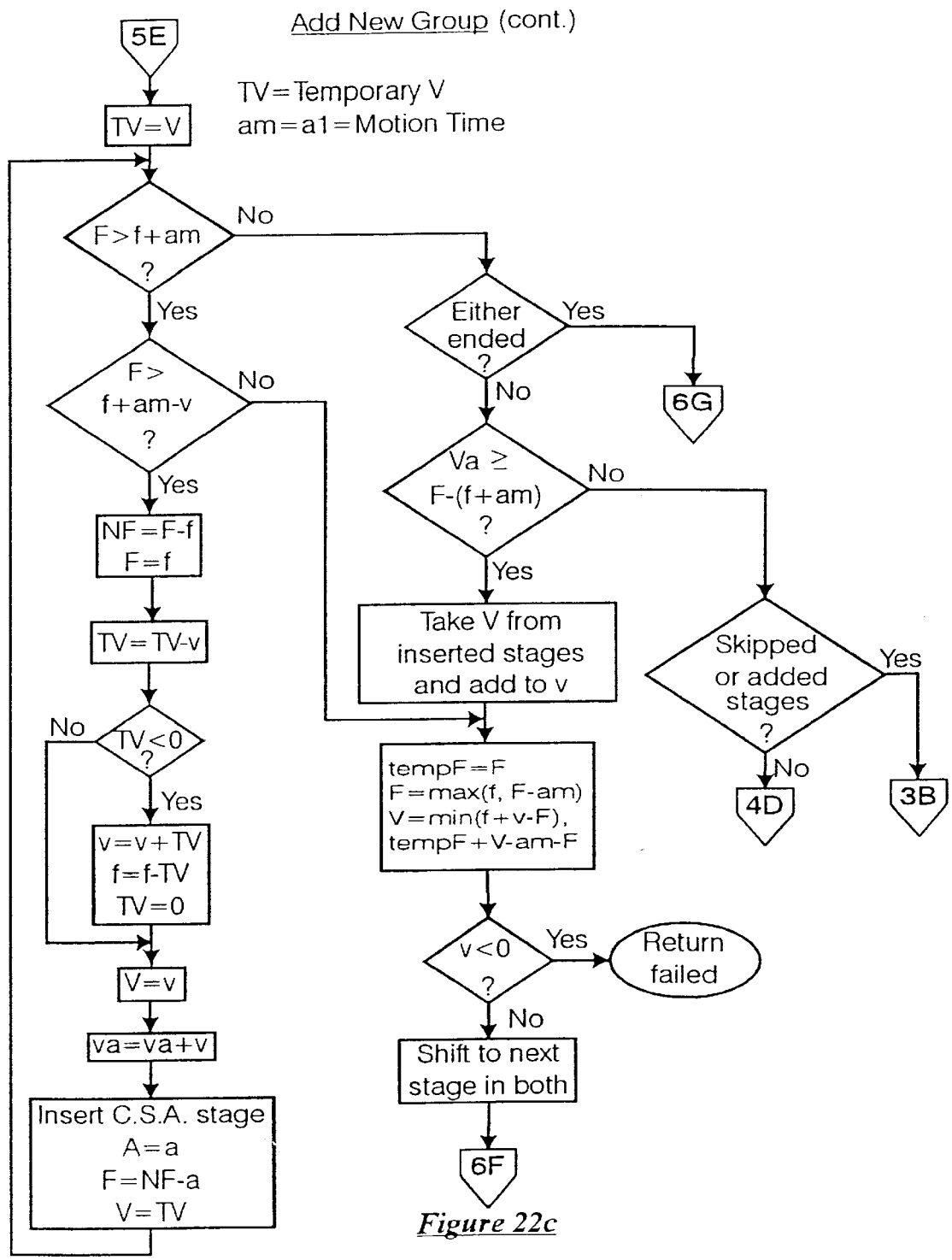
Figure 22D:
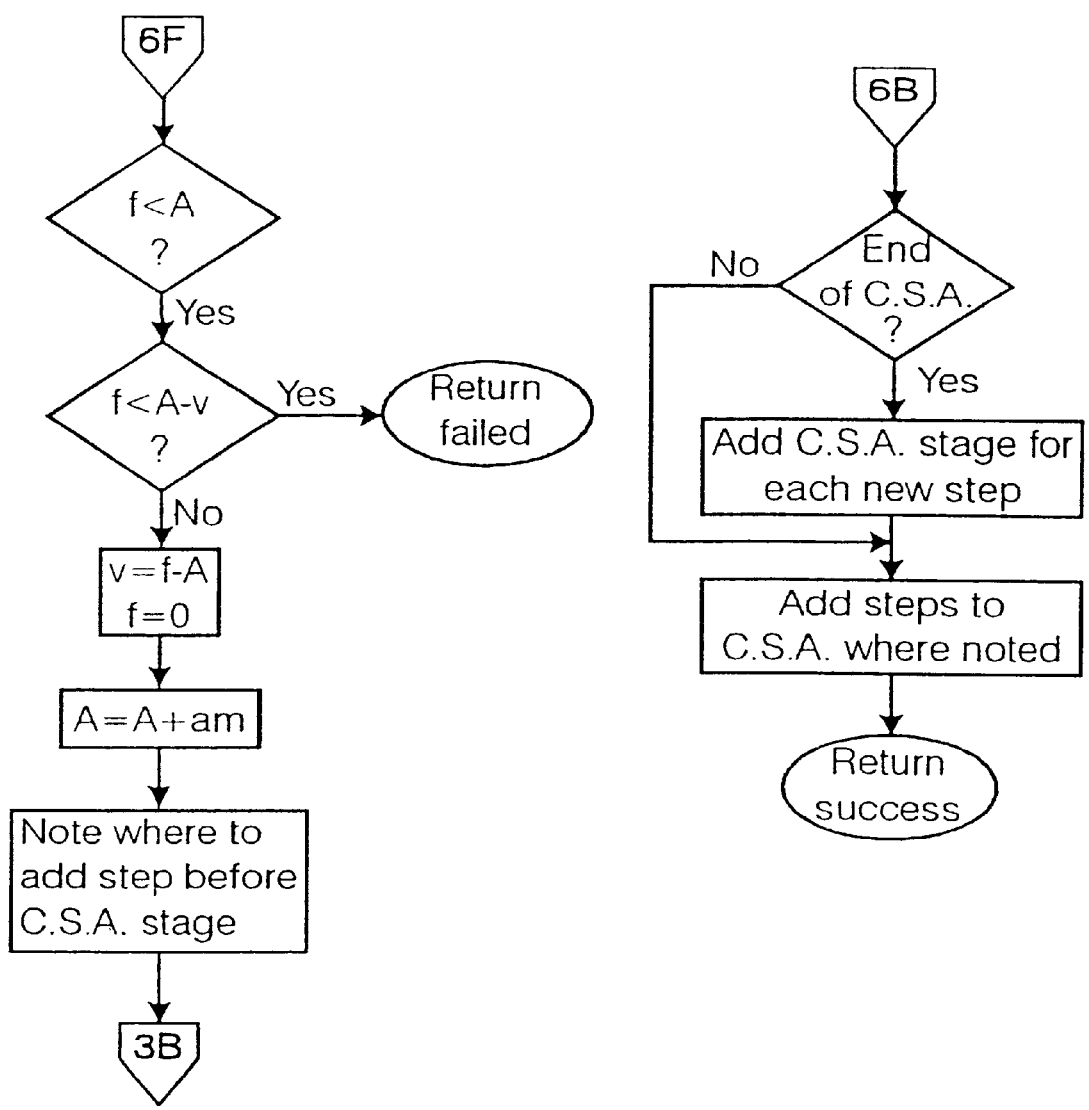

FIG. 21 illustrates a summary of how the autostainer control program calculates the most efficient dispensing pattern. Referring to FIG. 21, at step 2105 the control program first groups together the slides in each step that have the same reagents and same incubation times. The same protocol scheduling number is assigned to groups with the same incubation time. An array is created for each group that contains an action time (the amount of time required to pick up and dispense reagents), a fixed time (the incubation time that follows the action time), and a variable time (10% of the fixed time) for each protocol step.

At step 2110, a first group is selected as the "Currently Scheduled Array (CSA)." The control program then adds additional groups to the Currently Scheduled Array. At step 2115 an unscheduled group is selected. Next, at step 2120, the selected group is fitted into the Currently Scheduled Array by adding to the action times within the fixed and variable times. FIGS. 22a through 22d illustrate in detail how a group is added to a Currently Scheduled Array.

Step 2125 tests if the group fits into the Currently Scheduled Array. If it did not fit, the control program proceeds to step 2135 where it sees if it has tried to fit all the groups in the Currently Scheduled Array. If it has not tried to fit all the groups in yet, then it moves to step 2140 where another group is selected, and then back to step 2120 where it tries to fit that group in. If all groups have been tried, then the control program moves to step 2150 where it moves to the next stage in the Currently Scheduled Array and then back to step 2120 where it tries to fit that group in.

Referring back to step 2125 when a group fits into the schedule, the control program then tests if all the groups have been scheduled. If all the groups have not been scheduled then the control program proceeds back to step 2115 to schedule another unscheduled group. If all the groups have been scheduled as determined at step 2160, then the process is done.

Figure 23:
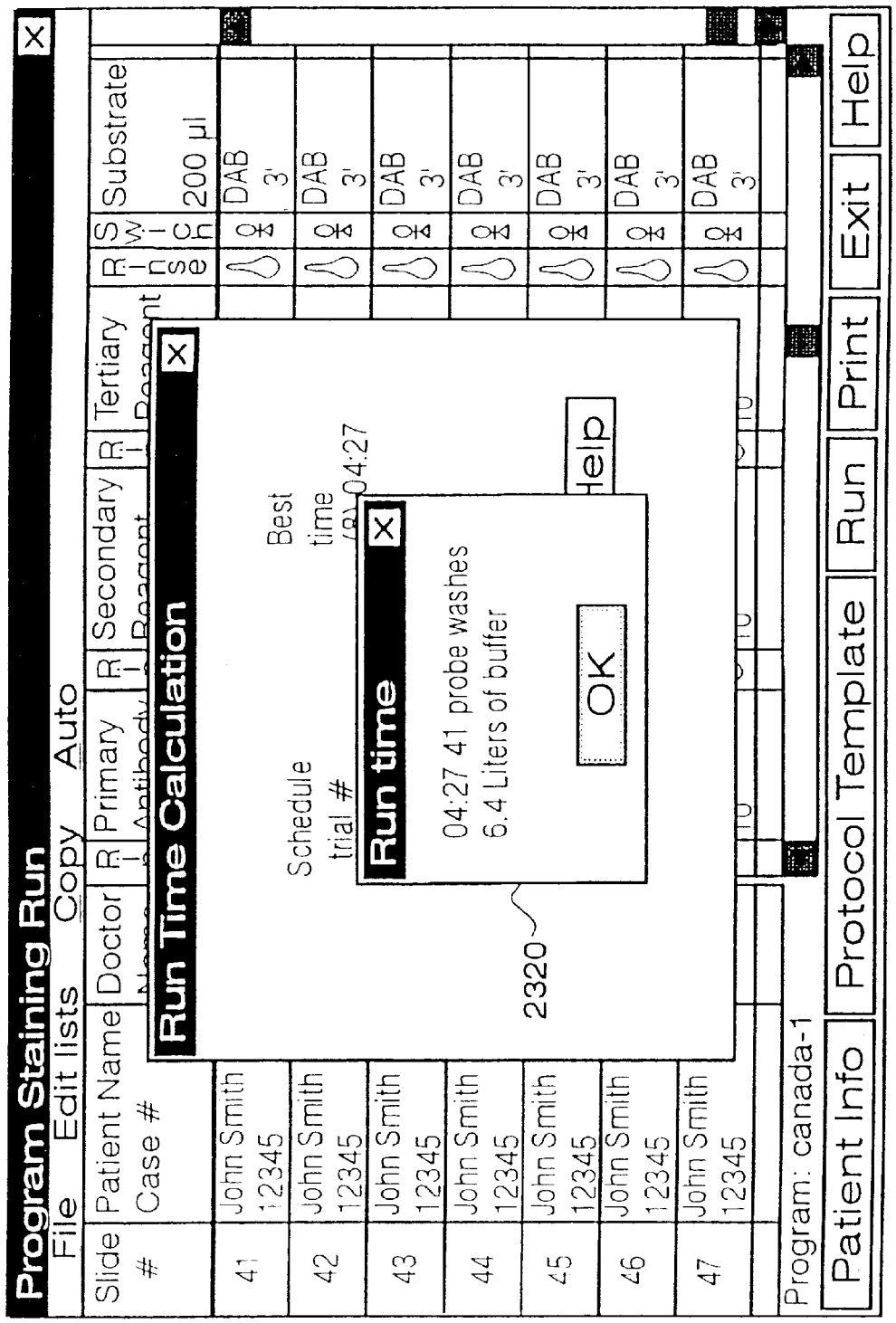
FIG. 23 illustrates the Run Time Calculation Window and the Run Time Dialogue Window of the autostainer control program.

While the autostainer control program calculates, the control program displays the number of tries and the best time in a Run Time Calculation screen, as illustrated in FIG. 23. When the autostainer control program is finished calculating the most efficient dispensing pattern, then a Run Time dialogue window is 2320 displayed. The Run Time dialogue window 2320 lists how long the staining run will take, how many times the probe will be washed, and how much buffer solution will be required for the staining run. The user clicks "OK" to proceed to the Reagent Layout Map screen.

Figure 24:
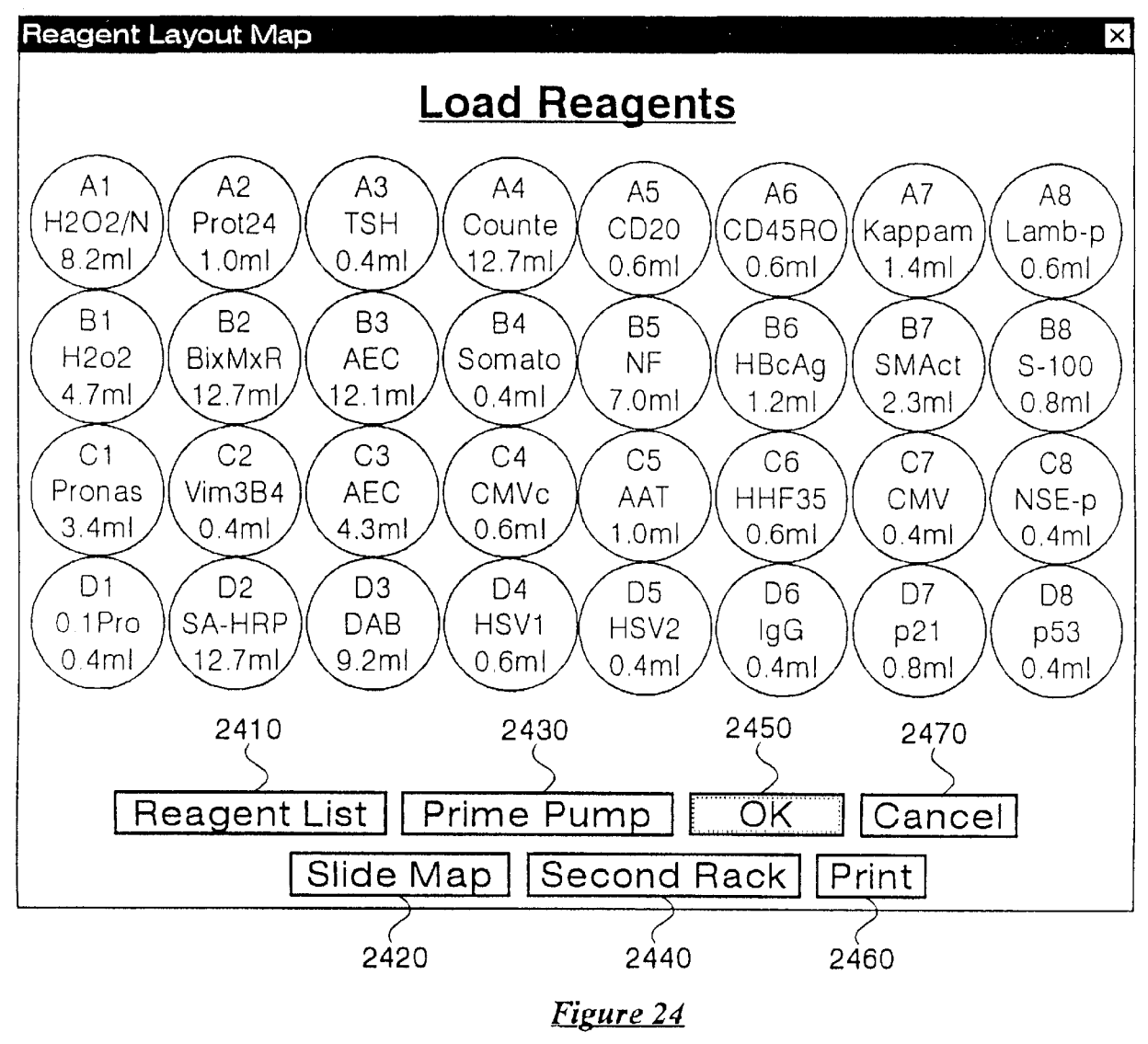

FIG. 24 illustrates the Reagent Layout Map screen of the autostainer control program. The Reagent Layout Map screen graphically displays a map of how the reagents should be loaded into the thirty-two vial reagent rack. Each vial is displayed with an alphanumeric rack position, the abbreviated reagent name, and the amount of reagent that is required.

Figure 25:
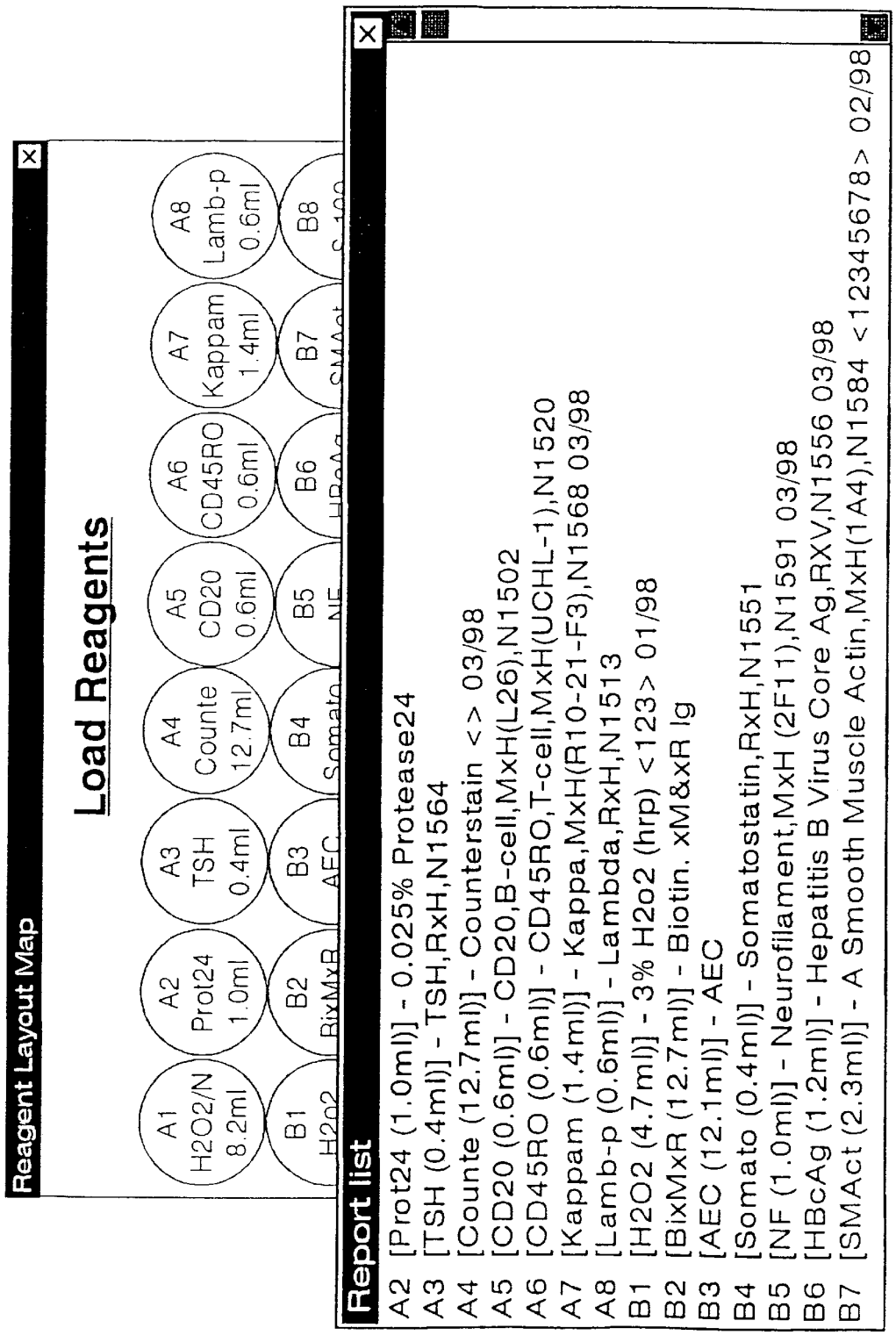
FIG. 25 illustrates the Reagent Layout Map Screen of the autostainer control program with a reagent list window displayed.

The Reagent Layout Map screen includes several function buttons. When the user selects the Reagent List button 2410, the reagent list appears as depicted in FIG. 25 and displays a detailed listing of the reagents used in the current staining run. Referring back to FIG. 24, the Prime Pump button 2430 primes the pump by allowing buffer solution to flow out of the wash head. The Cancel button 2470 cancels the current staining run and returns to the Program Staining Run screen. The Slide Map button 2420 returns to the previous Slide Layout Map screen. The Print button 2460 prints out the reagent layout map. The Second Rack button 2440 displays a second rack of the reagents. The Second Rack button 2440 only appears if there are so many reagents required in the current staining run that a second reagent rack is required. The OK button 2450 starts the current staining run. The user selects the OK button 2450 only after all the required reagents have been loaded into the reagent rack.

Figure 26:
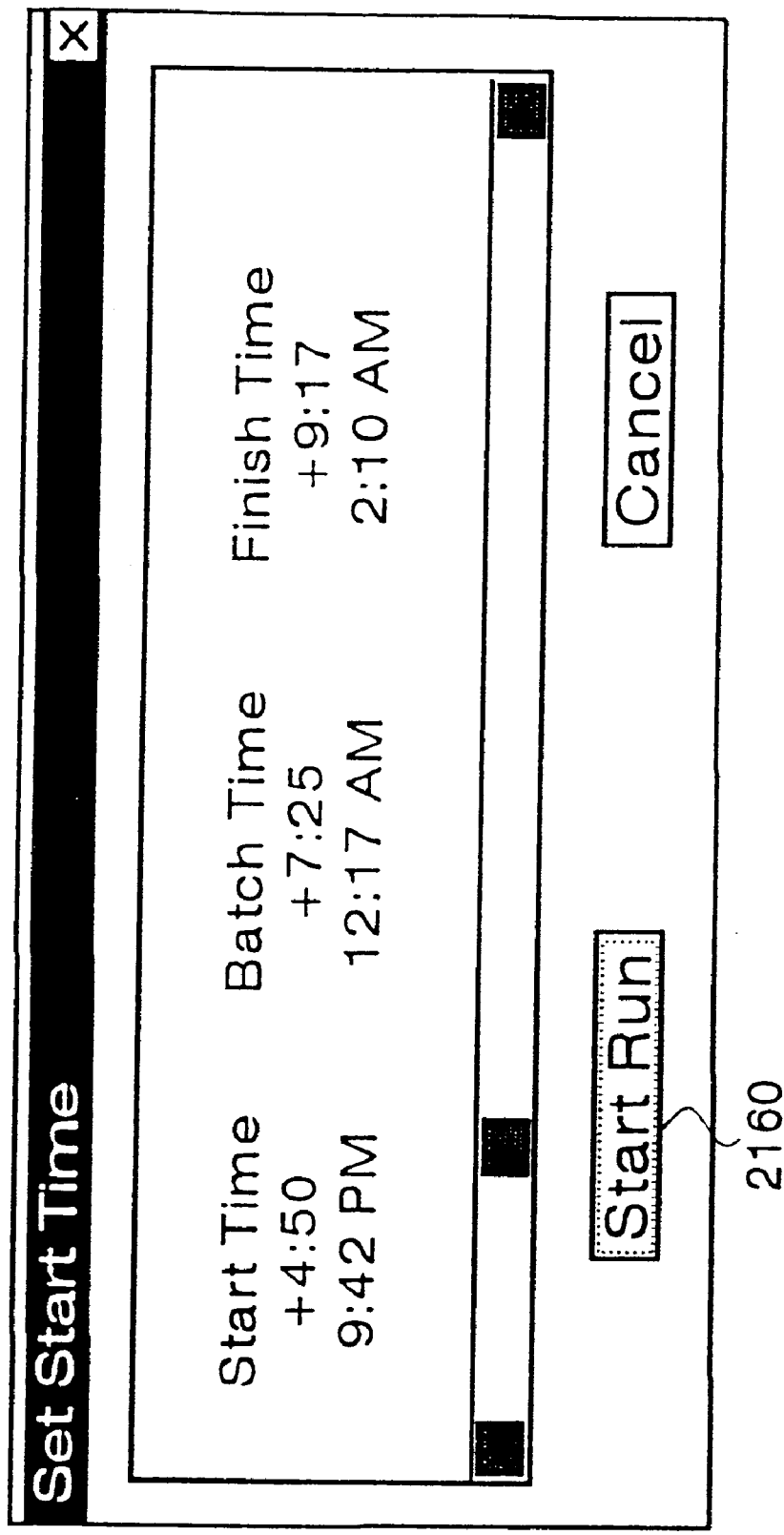
FIG. 26 illustrates the Set Start Time Window of the autostainer control program.

After selecting the OK button on the Reagent Layout Map screen, the autostainer displays a Set Start Time Window as illustrated in FIG. 26. The Set Start Time Window allows the user to select when the autostainer will begin the staining run. If the user selects a large delay, the autostainer control program will request additional buffer solution to keep the slides moist. When the user selects the Start button 2610, the autostainer control program begins the staining run. At this point the Run Log screen of FIG. 27 is displayed on the Control Program screen. The Run Log screen displays a detailed information log of the steps being performed along with a time stamp for each step. The Run Log screen displays the start time, the current time, and the projected finish time. To keep track of the current staining run, the Run Log screen displays the elapsed time, the projected remaining time, and the projected total run time.

The current staining run can be paused by selecting the "Emergency Stop" button 2710 on the Run Log screen. This will cause an "Are You Sure" dialogue window 2715 to be displayed. The dialogue window 2715 allows the current staining run to be resumed or aborted.

During the staining run, each slide is processed exactly as the protocol has been programmed for that slide. To avoid contamination, the autostainer head moves in between the reagent vials and glass slides after reagent has been picked up.

As stated earlier, the reagent probe includes custom circuitry that allows the probe to sense liquid levels. During a staining operation, this feature is used to determine if there is enough reagent. When there is not enough reagent to complete a staining run, the autostainer control program stops and a dialogue window appears which informs the user about the problem. If the user responds to the dialogue window, then the autostainer control program will move the Z head assembly out of the way and will display a Reagent Layout Map screen showing the type, amount, and location of the reagent to be added. This allows the user to correct the problem. If the user does not respond within a minute, then the autostainer control program will use what reagent is available and continue operation. The autostainer control program will soon again stop and warn the user of the insufficient reagent. Again, if there is no response from the user, the autostainer control program will continue the staining run without the needed reagent. When there is insufficient reagent to satisfy the immediate need, the autostainer control program will skip the slides that need the missing reagent and note that in the run log.

While the autostainer control program is performing the staining run, the personal computer can be used to run other programs as long as the autostainer control program is being executed on a multitasking operating system such as Windows® 95 from Microsoft® Corporation of Redmond, Wash. In one embodiment, separate functions are used to program a staining run and to run a staining run. Thus, while the staining run execution program is running, a user can execute the staining run programming function in order to program future staining runs.

After the staining run has completed, an "End Program Run" dialog box will be displayed and the computer will beep occasionally. At this point the user can print out a full copy of the program run log such that an Immunohistochemical Report can be created. The run information for any particular slide can be later recalled and used in conjunction with images of the stained slide captured with a CCD camera. Thus, a complete history of each slide will be available for analysis and diagnosis.

Stat Function

The Stat slide function of the autostainer allows the user to interrupt in-process staining of slides in order to initiate and stain one or more additional slides containing specimens that require immediate (stat) analysis, as disclosed in co-pending patent application Ser. No. 09/483,248, which is expressly incorporated by reference herein in its entirety. The overall process of programming Stat slides in an in-progress staining run is schematically shown in FIG. 28. During the staining run, the Increment Run Schedule Index, which refers to a counter that keeps track of which element in an array of pointers is the current pointer, is constantly updated. Each pointer points to another type of array containing pointers to link lists of actions that the instrument must perform in order to stain the slides. Incrementing the Run Schedule Index prepares the program to start processing the steps for the next sub-schedule and/or the addition of a slide or slide groups. This enables a user to determine if the schedule is interruptible when the user selects the Stat slide function.

In reference to FIG. 29, if the staining program that was already in progress when the Stat function was selected had also enabled the Stat function, the previous Stat function is disabled and the "New Program" and "Review Program" functions are enabled. If the Stat function had not been previously enabled, the "New Program" and "Review Program" functions are disabled. Upon initiation of the Stat function, the "Stat Slides" button displays the time remaining before the current program, in progress, can be interrupted and processing of the new Stat slides can be initiated.

FIG. 30 shows the "Timer Message" routine, which is displayed when the Stat function is enabled. This routine calculates the time until the next interruption point, converts it to hours and minutes, and displays it on the "Stat Slides" button. Other times are then subsequently updated, including the length of time that the staining run has been in process, the length of time until the current run is finished, the beginning, projected completion, and total staining run time, and the current time. When both of the functions in FIGS. 29 and 30 are completed, the program returns to the routine in FIG. 28. When all the slides are in rinse buffer the user sees the prompt "Ready For Stat Slides", and must select whether he or she wishes to interrupt the current program to include the stat slides.

If the user selects "NO", or ten minutes elapse with no user response, staining of the pending slides continues. If the user selects "YES", the program then hides the Run Log and displays the Main Programming grid. The user can then begin programming the stat slides, following a programming procedure as previously described (Creating a Staining Run). The programming procedure includes functions of defining protocol templates and methods, changing reagent dispensing locations and volumes, and adding new reagents.

When the user has finished programming the added slides, the program then initiates several routines to group the pending and added slides according to identical or aligned protocols, and then schedules the Stat slides for the staining run. These routines are schematically illustrated in FIGS. 31 and 32a–32g, with an option whether to complete processing of the Stat slides before, or concurrently with, the pending slides.

If Stat slides are added to the schedule, the program is restarted (Disable Delayed Start) and returns to the Begin Staining Run routine, shown at 1A in FIG. 28. If Stat slides are not added to the schedule, the program returns to the original schedule and continues staining slides from the point at which it was previously interrupted.

Figure 31:
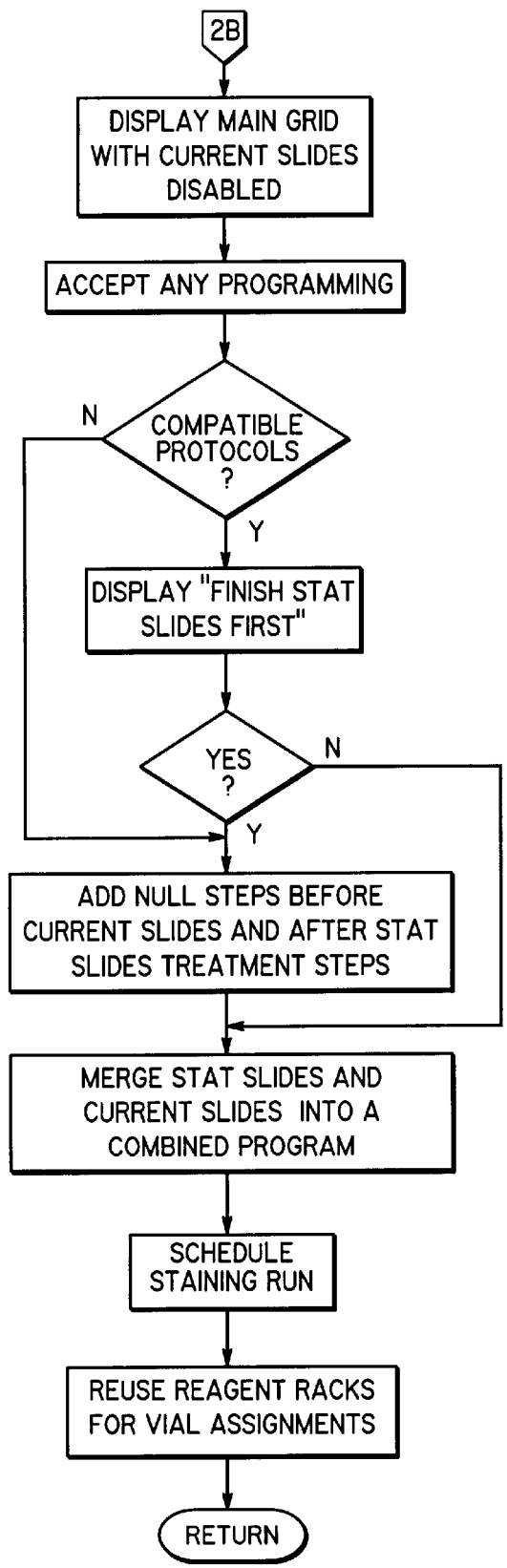
FIG. 31 illustrates additional steps in implementing a Stat staining program.

With reference to FIG. 31, beginning at 2B, the main grid is displayed and accepts programming for groups of slides, as previously described (Creating a Staining Run). If the programming that has been selected is compatible with the current protocol, now interrupted, the program inquires whether the user wishes to complete the Stat slides first by displaying "Finish Stat Slides First?" or another similar query. If the user wishes to complete staining of Stat slides first, or if the protocols are not compatible with any of the current protocols, the program then adds null steps, both before any currently pending groups and after the newly added Stat slide treatment steps, to allow the Stat slide groups to be completed before any other slide groups. If the user does not wish to complete the Stat slide groups first, the Stat slide groups are merged with the current slide groups in a combined program, to stain both the pending slide groups and the Stat slide groups. The program then schedules the staining run, shows the assignment of reagents for the run reusing the reagents racks for vial assignments, and returns to the routine shown in FIG. 28 at 2B.

Figure 32A:
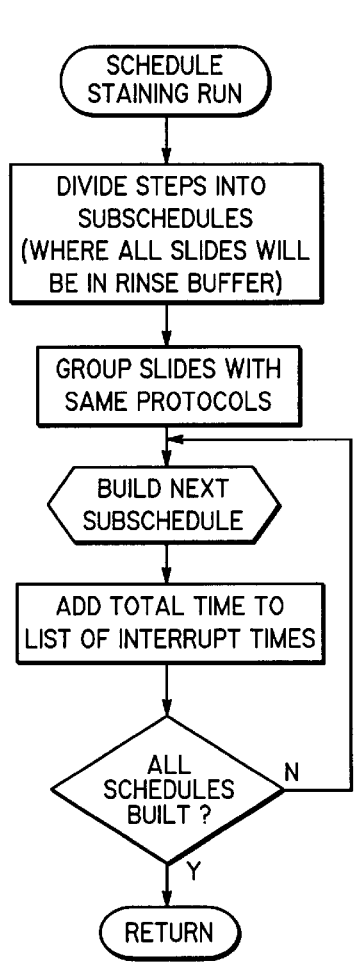
FIGS. 32a–32g illustrates embodiments for programming Stat slides.

FIG. 32a shows further details of a staining run. To schedule a staining run, the staining steps are divided into sub-schedules, each sub-schedule terminating with all slides incubated in rinse buffer. The slides to undergo the same staining protocols are then grouped. The program calculates the total staining time for each sub-schedule, which is then added to the list of possible "interrupt" times. The program continues this process for each group. Once all the sub-schedules are built, the program then returns to the next function (Reagent Vial Allocation, adding the volumes of reagents required to complete the staining run, and assigning the volumes to reagent vials, as previously described (Creating a Staining Run)).

Figure 32B:
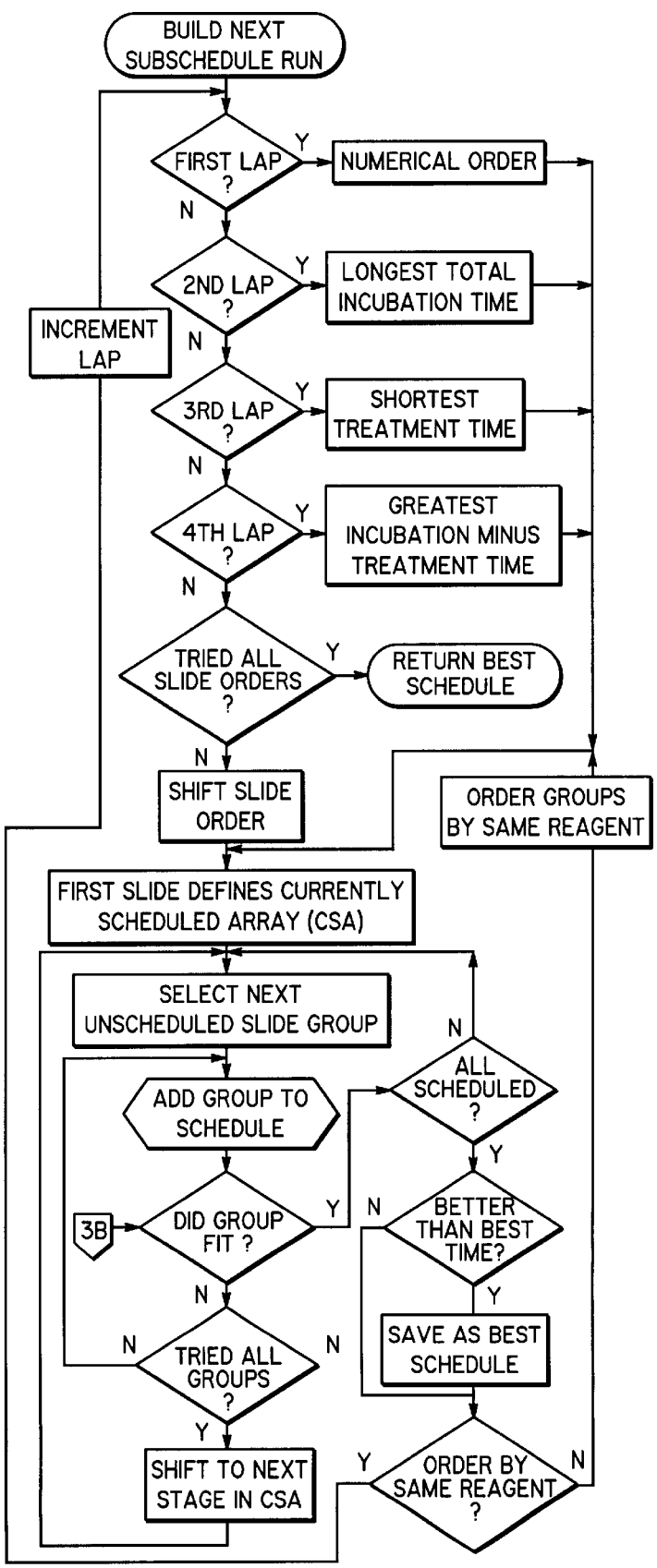

FIG. 32b shows how the sub-schedules are built. The sub-schedules are divided into "laps." In the first lap, the slide groups are ordered numerically. Once the first lap is completed, the second lap is initiated, in which the slide groups are ordered by incubation time, with the longest incubation time first, for the specific desired staining protocol. Once the second lap is completed, the third lap is initiated, in which the slide groups are ordered by treatment time, with the shortest treatment time first, for the specific desired staining protocol. Once the third lap is completed, the fourth lap is initiated, in which the slide groups are ordered by the difference of incubation time minus treatment time (incubation time-treatment time), with the greatest difference first. With reference to FIG. 32b, after the fourth lap, subsequent laps start with the best schedule from the first four laps and rotate the order of the slide groups by moving the first group to the end and shifting the other groups up one.

For each lap, the steps required to treat the first group of slides are assigned as the initial entries in the Current Scheduled Array (CSA). The program then selects the next unscheduled slide group and attempts to add it to the schedule. If the group does not fit into the schedule, and if all the groups were not yet tried, the next group is tried. If all of the groups were tried in the schedule, there is a shift to the next stage in the Current Scheduled Array and the scheduling process is repeated. The effect of shifting to the next stage usually results in groups that have already been scheduled being incubated and rinsed before the next group of slides is treated. If the group does fit into the schedule, and if all the slide groups are not accounted for nor scheduled, the program then repeats the procedure until all the slide groups are accounted for.

Figure 32C:
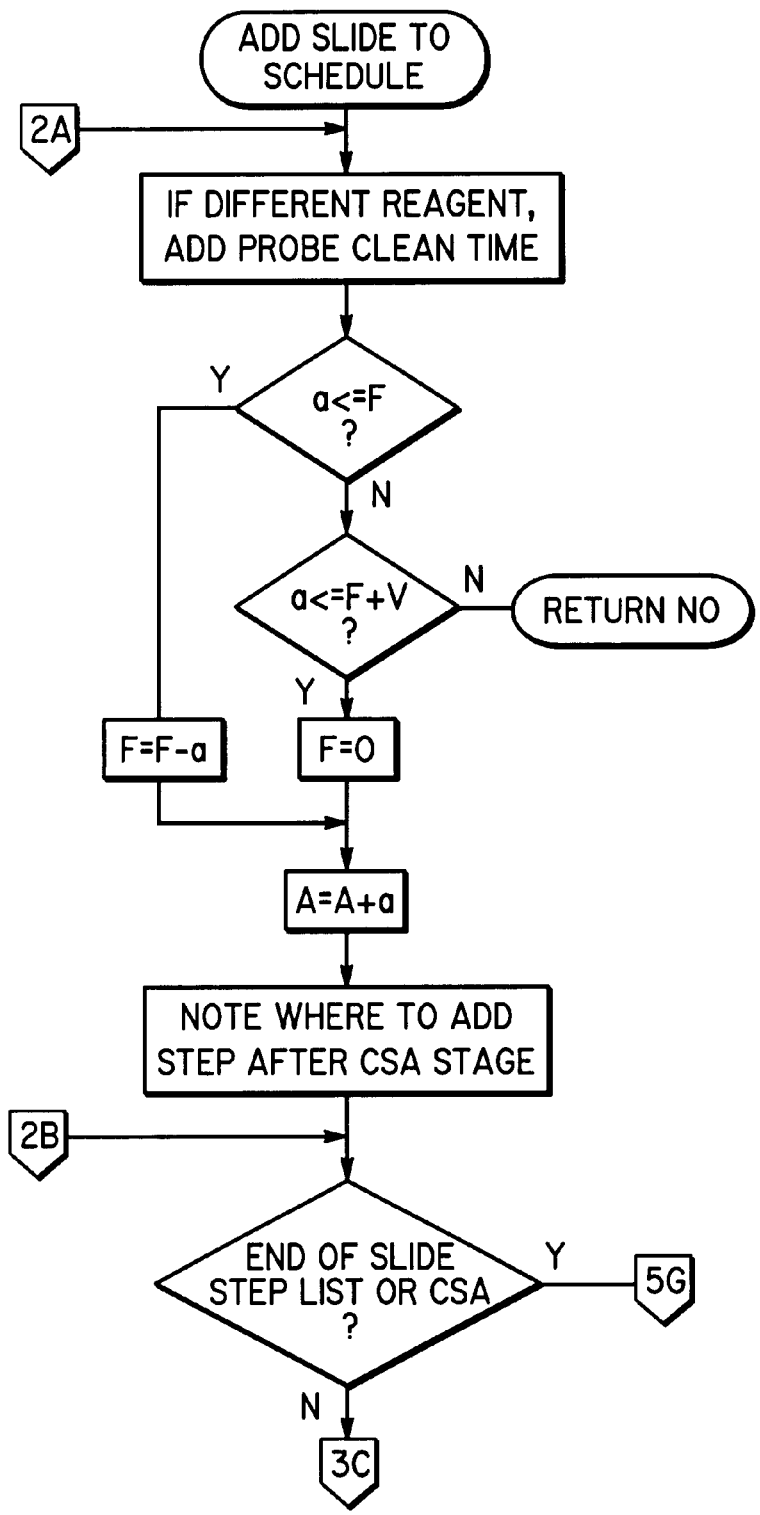

Once all the slide groups are scheduled, including those groups that contain additional or Stat slides, the program then compares staining times for all the groups to the best-known time, and selects the best schedule. For each ordering of groups, an alternate order is created by combining groups with the same reagent. "Combining groups" means making them consecutive, although not necessarily treating them as the same group. The first group of a combined group consist of slides from the original order of the groups, that is, slides that were pending at the point of interruption. Subsequent groups in the combined groups are selected as those using the same reagent, regardless of their positions in the original order. FIG. 32c, beginning at 2A, shows the routine to achieve the Current Scheduled Array by adding a slide, or slide group, to the schedule. The schedule starts with the first group from the ordered list. Subsequent groups are added to the schedule, where they will fit without violating the limits of incubation times for all groups already scheduled. If the reagents for the next group to be added are different, the program adds time required for cleaning the reagent probe to accommodate the new reagents ("probe clean time"), and then the program checks whether the new group action time (a), is less than or equal to the current schedule fixed time F (the incubation time that follows the action time). If the new group action time (a) is not less than or equal to the current schedule fixed time, the program then checks whether the new group action time (a) is less than or equal to the current schedule fixed time (F) plus current schedule variation time (V). If the new group action time (a) is not, the program returns the result NO, because it does not fit, and returns to 3B in FIG. 32b. If the new group action time (a) is less than or equal to the current schedule fixed time (F) plus the current schedule variation time (V), the current schedule fixed time (F) is set equal to zero. Alternatively, at the outset, if the new group action time (a) is less than or equal to the currently schedule fixed time (F), the currently schedule fixed time (F) becomes equal to itself minus the new group action time (a), and the program continues.

At this point, the current schedule action time (A) is recalculated by adding the new group action time (a) to the existing current schedule action time (A). The program indicates where to add the step to accommodate the Stat slide group after the Current Scheduled Array. If the program is at the end of a particular slide group step list (i.e., the list of functions to perform), or is at the end of a Current Scheduled Array, the routine beginning at 5G in FIG. 32g, is initiated. If not, the routine beginning at 3C in FIG. 32d is initiated.

Figure 32D:
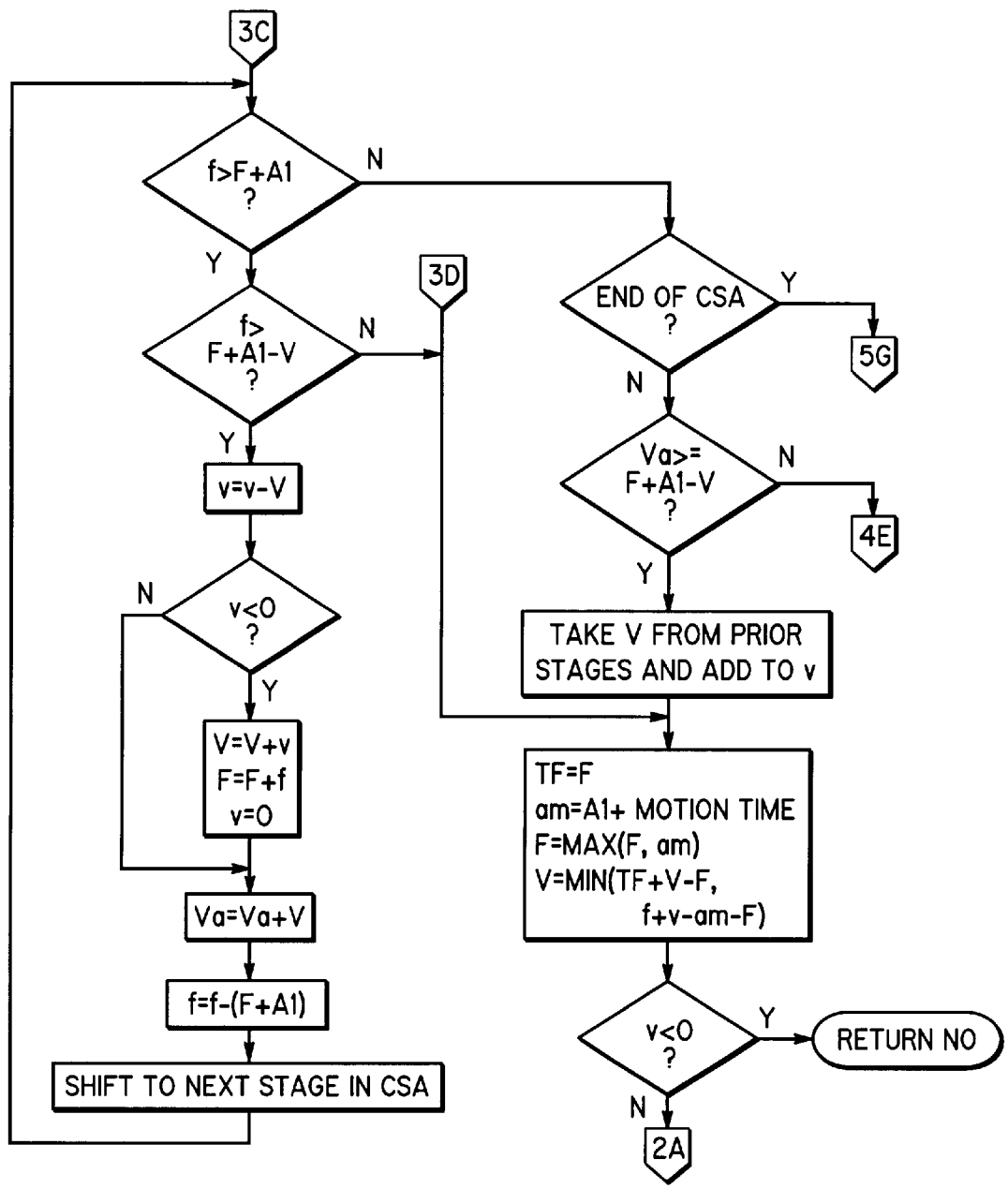

With reference to FIG. 32d, beginning at 30, the program first questions whether the new group fix time (f) is greater than the current schedule fixed time (F) plus the current schedule action time for the next stage (A1). If it is not, the program then queries whether it is at the end of a Current Scheduled Array and, if so, goes to the function beginning at 5G in FIG. 32g. If it is not at the end of a Current Scheduled Array, the program then queries whether the accumulated current variable time (Va) is greater than or equal to the current schedule variable time (F) plus the current schedule action time for the next stage (A1) minus the current schedule variable time (V) for the new slide group. If it is not greater than or equal to this number, the program then follows the function shown beginning at 4E in FIG. 32e. If it is greater than or equal to this number, the program then takes the current schedule variable time (V) from the prior stages and adds it to the new group variable time (v). The program (1) sets the temporary current schedule fixed time (TF) to the current schedule fixed time (F); (2) sets the current schedule action time for the next stage plus motion time (am) by adding the current schedule action time for the next stage (A1) to the motion time, (3) calculates the current schedule fixed time (F) as a function of the maximum of the current schedule fixed time and current schedule action time for the next stage plus motion time (am), and (4) calculates the current schedule variable time (V) as a function of the minimum of the temporary current schedule fixed time (TF) plus the current schedule variable time (V) minus the current schedule fixed time (F), and the new group fixed time (f) plus the new group variable time (v) minus current schedule action time for the next stage plus motion time (am) minus the current schedule fixed time (F). The program determines whether the new group variable time (v) is less than zero. If it is, the program then returns the results NO, indicating that it did not fit the schedule, and returns to 3B in FIG. 32b. If it is not, the program then initiates the events beginning at 2A in FIG. 32c.

If the new group fixed time (f) is greater than the current schedule fixed time (F) plus the action time for the next stage (A1), as shown beginning at 3C in FIG. 32d, the program then queries whether the new group fixed time (f) is greater than the current schedule fixed time (F) plus the current schedule action time for the next stage (A1) minus the current schedule variable time (V). If it is not greater, the program then follows the function beginning at 3D, previously described. If it is greater, the program then sets the new group variable time (v) equal to the new group variable time (v) minus the current schedule variable time (V). The program queries whether the new group variable time (v) is less than zero. If it is, the program resets (1) the current schedule variable time (V) equal to V plus the new group variable time (v), (2) the current schedule fixed time (F) equal to F plus the new group fix time (f), and (3) the new group variable time (v) equal to zero. At this point, or if the new group variable time (v) is not less than zero, the program sets the accumulated current variable time (Va) by adding Va plus the current schedule variable time (V), and sets the new group fix time (f) equal to (f) minus the current schedule variable time (F) plus the action time for the next stage (A1). The program then skips to the next stage in the Current Scheduled Array.

Figure 32E:
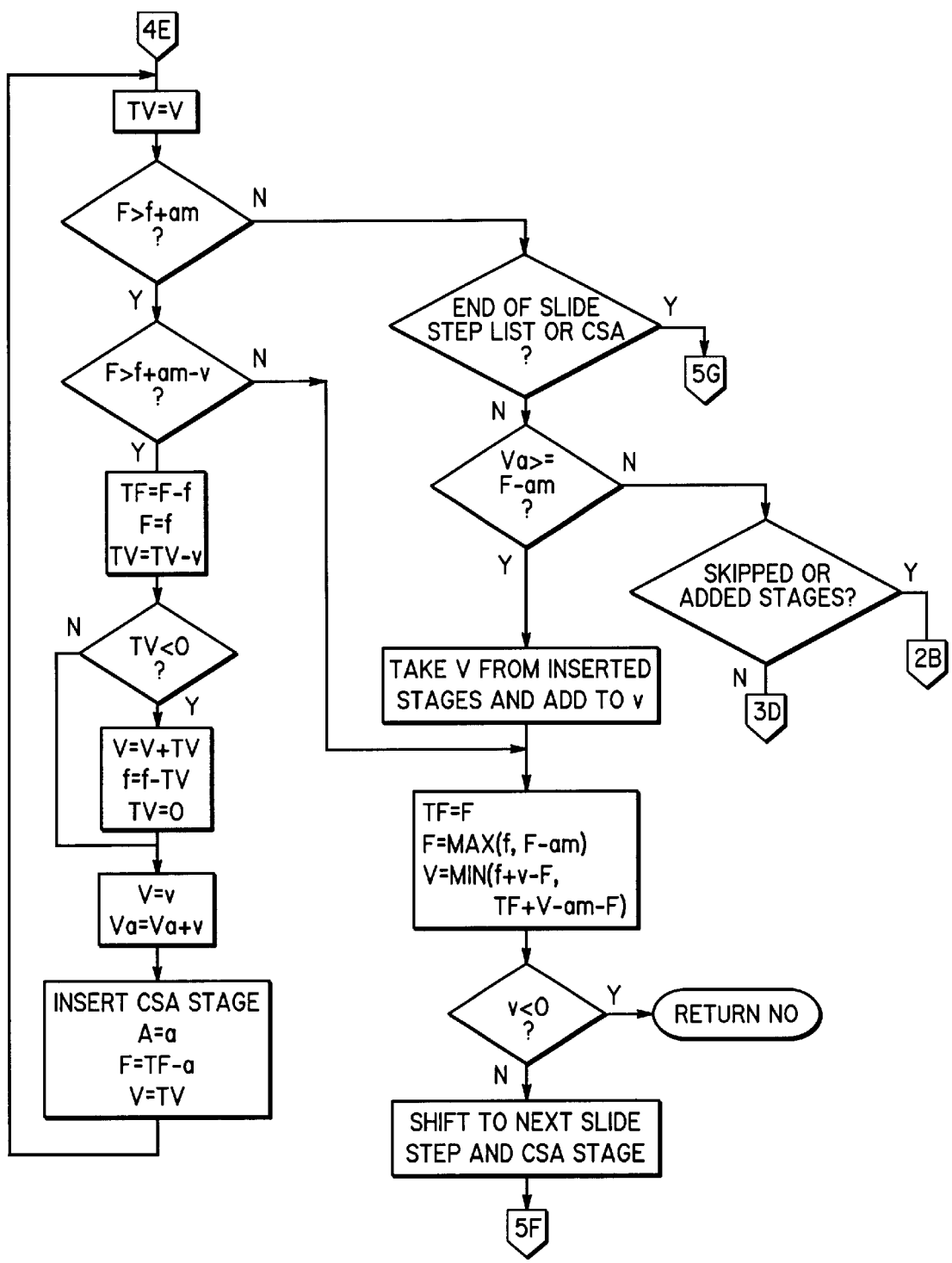
Figures 32F, 32G:
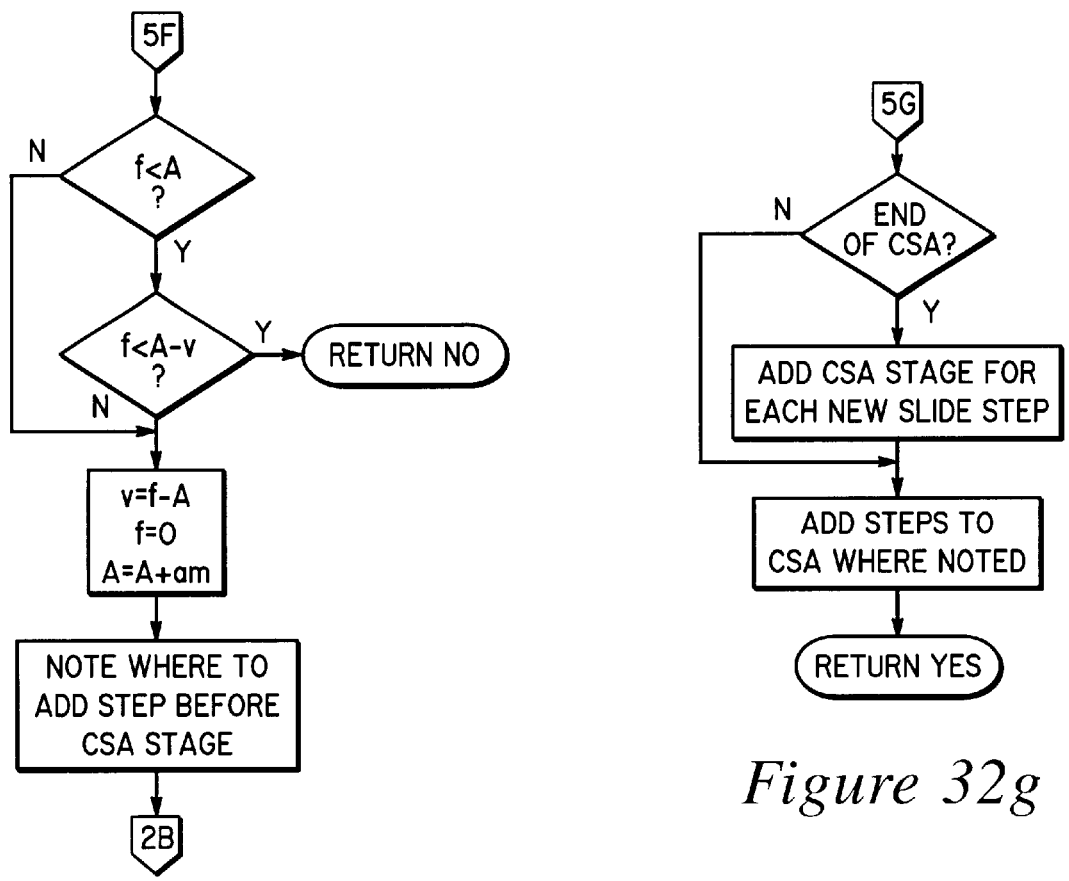

If the accumulated current variable time (Va) is not greater than or equal to the current schedule fixed time (F) plus A1 minus the current schedule variable time (V), the program then initiates the routine beginning at 4E in FIG. 32e. The temporary current schedule variable time (TV) is set as the current schedule variable time (V). If the current schedule fixed time (F) is greater than the new fixed time (f) plus the new group action time for the next stage plus motion time (am), and if F is also greater than f plus am minus the new group variable time (v), then (1) the temporary current schedule fixed time (TF) is set equal to the current schedule fixed time (F) minus the new fixed time (f), (2) F is set equal to f, and (3) the temporary current schedule variable time (TV) is reset to TV minus the new group variable time (v). If TV is less than zero, (1) v is reset to v plus TV, (2) f is reset to f minus TV, (3) TV is set equal to zero, (4) the current schedule variable time (V) is set equal to the new group variable time (v), and (5) the accumulated variable time (Va) is reset to Va plus v. If TV is not less than zero, then steps (4) and (5) are followed. A new Current Schedule Array stage is then inserted and (1) the current schedule action time (A) is set equal to the new slide action time (a), (2) F is reset equal to TF minus a, and (3) V is reset to equal TV.

With reference to FIG. 32e when F is not greater than f plus am, and the input is at the end of the Slide Step List or Current Schedule Array (End of Slide Step List or CSA), the routine beginning at 5G in FIG. 32g is initiated. If it is not at the end of the Slide Step List or Current Schedule Array, and Va is not equal to or greater than F minus am, and there are no skipped or added stages, then the routine beginning at 3D in FIG. 32d is initiated. If there are skipped or added stages, then the routine beginning at 2B in FIG. 31 is initiated.

If Va is greater than or equal to F minus am, then the current schedule variable time (V) from the inserted stages is added to the new group variable time (v). This is followed by (1) resetting TF to equal F, (2) resetting F to equal the maximum of the function of the new group fixed time (f) and F minus am, and (3) resetting V to equal the minimum of the function of the new group fixed time (f) plus v minus F, and TF plus V minus am minus F. Earlier in routine 4E (of FIG. 32e), if F is not greater than f plus am minus v, then previous steps (1), (2) and (3) are performed. If the new group variable time (v) is less than zero, then the program returns the result NO, because the group did not fit, and returns to routine 3B in FIG. 32b. If the new group variable time (v) is not less than zero, then the program (1) shifts to the Next Slide Step and Current Schedule Array stage, and (2) initiates the routine beginning at 5F in FIG. 32f.

With reference to the routine beginning at 5F, the initial query is whether the new group fixed time (f) is less than the current schedule action time (A). If the answer is yes, then the query is whether the new group fixed time (f) is less than the current schedule action time (A) minus the new group variable time (v). If the answer to this second question is yes, then the program returns the result NO, because the group did not fit, the program returns to the routine beginning at 3B in FIG. 32b. If it is not, or if the answer is no to the question at the beginning of 5F, then (1) the new group variable time (v) is set equal to the new group fixed time (f) minus the current schedule action time, (2) the new group fixed time (f) is set to zero, and (3) the current schedule action time (A) is reset to A plus the new group action time for the next stage plus the motion time (am). The program then notes where to add the step before the Current Schedule Array and returns to the routine beginning at 2B in FIG. 31.

When the routine beginning at 5G in FIG. 32g is initiated, and the function is at the end of the Current Scheduled Array, then the array stage for each new slide is added (Add GSA Stage for Each New Slide Step). Specifically, the steps beginning at 2A in FIG. 32c, and beginning at 5F in FIG. 32f, are appended to their corresponding steps in the Current Schedule Array, a YES result is returned, and the routine returns to 3B in FIG. 32b. If it is not the end of the Current Schedule Array, then all new steps are added to the Current Schedule Array, a YES result is returned, and the routine returns to 3B in FIG. 32b.

The foregoing has described a method and apparatus for automatic tissue and cell preparation staining. It is contemplated that changes and modifications may be made by one of ordinary skill in the art, to the materials and arrangements of elements of the present invention without departing from the scope of the invention.

What is claimed is:

1. A method of operating an autostainer having a computer system comprising:

providing a first processing protocol for processing a plurality of first slides;

determining a first processing schedule for said plurality of first slides from said first processing protocol;

processing said plurality of first slides according to said first processing schedule with the autostainer;

providing a computer usable medium having computer readable code embodied therein for interrupting the processing of said plurality of first slides before completion of said first processing schedule;

specifying a second processing protocol for at least one second slide; and determining a second processing schedule from said first processing protocol and said second processing protocol; and resuming the processing of said plurality of first slides and said at least one second slide according to said second processing schedule.

2. The method of claim 1, wherein the step of determining said second processing schedule includes comparing the compatibility of said second processing protocol with said at least one first processing protocol.

3. The method of claim 1, further wherein the step of resuming the processing further comprises processing said second slide before processing said plurality of first slides.

4. The method of claim 1 wherein the step of resuming the processing further comprises processing said plurality of first slides and said second slide concurrently.

5. The method of claim 1 wherein the step of specifying said second processing protocol further comprises selecting a plurality of slide preparation steps using a graphical user interface.

6. The method of claim 1 further comprising, before the step of determining said second processing schedule, the steps of:

displaying reagent information for said second processing protocol; and providing additional reagents appropriate for accomplishing said second processing schedule.

7. The method of claim 1 further comprising:

providing a computer program product for use with a computer system on an autostainer comprising usable medium having first computer readable code to select a processing protocol for said at least one second slide, schedule processing of said plurality of first slides and said at least one second slide to generate a processing schedule, and enable processing of said plurality of first slides and said at least one second slide.

8. The method of claim 7 further comprising enabling a stat function and thereafter determining a time in said processing for processing said at least one second slide.

9. The method of claim 8, further comprising providing means for selecting whether to process at least one second slide prior to or concurrently with said first slides.

10. The method of claim 7, wherein said means to select processing protocols for said at least one second slide comprises selecting methods and reagents for said at least one second slide.

11. The method of claim 7, wherein said means to schedule processing of said first slides comprises determining compatible processing protocols among said first slides and said at least one second slide; grouping slides for processing; forming sub-schedules for the slide groups; and determining a time to initiate processing from the sub-schedules.

12. The method of claim 7, wherein said means to enable processing of said first slides comprises processing said first slides according to said processing schedule.

13. A computer program product for in-process interruption of staining a plurality of slides in an autostainer having a computer system comprising:

a first computer readable code operable to process a plurality of first slides according to a first processing schedule from a first processing protocol, a second computer readable code operable to interrupt said first processing schedule, a third computer readable code operable to select a second processing protocol for a second slide, a fourth computer readable code operable to generate a second processing schedule from said first protocol and said second protocol, and a fifth computer readable code operable to enable processing of said plurality of first slides and said second slide according to said second processing schedule; and a computer readable medium that stores said first, second, third, fourth and fifth computer readable codes and is operable with the computer system of the autostainer.

14. The product of claim 13, wherein second computer readable code further comprises computer-readable instructions enabling a stat function.

15. The product of claim 14, further comprising a sixth computer readable code operable to select whether to process said second slide prior to or concurrently with said plurality of first slides, said computer readable medium further storing the sixth computer readable code.

16. The product of claim 13, wherein said third computer readable code further comprises computer-readable instructions for selecting a method and at least one reagent for said second processing protocol.

17. The product of claim 13, wherein said fourth computer readable code further comprises:

computer-readable instructions for comparing said first protocol and said second protocol;

computer-readable instructions for grouping slides according to the result of the step of comparing in a plurality of slide groups for processing;

computer-readable instructions for forming sub-schedules from said slide groups; and computer-readable instructions for determining a time to initiate processing of said plurality of first slides and said second slide according to the sub-schedules.

18. An autostainer comprising:

an automatic staining apparatus having capacity for a plurality of slides and dispensing reagents onto said slides, said autostainer responsive to a set of electrical commands, said plurality of slides comprising a first set of slides, a second set of slides, and at least one stat slide;

a computer system coupled to said autostainer for delivering said set of electrical commands; and an autostainer control program executing a first set of programmable protocol steps for said first set of said slides, a second set of programmable protocol steps for said second set of said slides, and a set of programmable protocol steps to interrupt said protocol steps for said first set and second set of said slides and include said at least one stat slide in said set of programmable protocol steps.

19. The apparatus of claim 18, further comprising an autostainer protocol editor program, said autostainer protocol editor program for programming said first and said second set of programmable protocol steps for said first set and said second set of said slides, respectively.

* * * * *